(12) United States Patent
Gerber

(10) Patent No.: US 9,272,140 B2
(45) Date of Patent: Mar. 1, 2016

(54) METHOD, SYSTEM AND DEVICE FOR TREATING DISORDERS OF THE PELVIC FLOOR BY ELECTRICAL STIMULATION OF THE SACRAL AND/OR PUDENDAL NERVES

(75) Inventor: Martin T. Gerber, Maple Grove, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 2224 days.

(21) Appl. No.: 12/059,243

(22) Filed: Mar. 31, 2008

(65) Prior Publication Data
US 2008/0183236 A1    Jul. 31, 2008

Related U.S. Application Data

(63) Continuation of application No. 10/836,924, filed on Apr. 30, 2004, now Pat. No. 7,369,894, which is a continuation-in-part of application No. 10/236,578, filed on Sep. 6, 2002, now abandoned, and a (Continued)

(51) Int. Cl.
*A61N 1/36*  (2006.01)
*A61N 1/05*  (2006.01)

(52) U.S. Cl.
CPC .......... *A61N 1/36007* (2013.01); *A61N 1/0507* (2013.01); *A61N 1/0551* (2013.01); *A61N 1/36071* (2013.01); *A61N 1/36107* (2013.01); *A61N 1/0521* (2013.01)

(58) Field of Classification Search
USPC .......................... 607/40, 41, 46, 117, 118, 148
See application file for complete search history.

(56) References Cited

U.S. PATENT DOCUMENTS

| | | |
|---|---|---|
| 3,902,501 A | 9/1975 | Citron et al. |
| 4,106,512 A | 8/1978 | Bisping |
| 4,406,288 A | 9/1983 | Horwinski et al. |
| 4,476,868 A | 10/1984 | Thompson |
| 4,566,063 A | 1/1986 | Zolnowsky et al. |
| 4,607,639 A | 8/1986 | Tanagho et al. |

(Continued)

FOREIGN PATENT DOCUMENTS

| | | |
|---|---|---|
| EP | 0 245 547 | 11/1987 |
| WO | WO 02/078592 | 10/2002 |

OTHER PUBLICATIONS

Juenemann et al., "Clinical Significance of Sacral and Pudendal Nerve Anatomy," The Journal of Urology, vol. 139, pp. 74-80 (Jan. 1988).

(Continued)

*Primary Examiner* — Theodore Stigell
*Assistant Examiner* — Natasha Patel
(74) *Attorney, Agent, or Firm* — Shumaker & Sieffert, P.A.

(57) ABSTRACT

Described are implantable devices and methods for treating various disorders of the pelvic floor by means of electrical stimulation of tissue volumes at two or more locations adjacent sacral nerves or portions thereof, and/or pudendal nerves or portions thereof. Two or more electrical stimulation regimes are applied on a continuous, alternating, intermittent or other basis to the respective tissue volumes in an amount and manner effective to treat a number of disorders, including, but not limited to, urinary and/or fecal voiding dysfunctions such as constipation, incontinence disorders such as urge frequency and urinary retention disorders, sexual dysfunctions such as orgasmic and erectile dysfunction, pelvic pain, prostatitis, prostatalgia and prostatodynia.

18 Claims, 18 Drawing Sheets

Related U.S. Application Data continuation-in-part of application No. 10/723,316, filed on Nov. 26, 2003, now Pat. No. 7,328,068, said application No. 10/836,924 is a continuation-in-part of application No. 10/723,903, filed on Nov. 26, 2003, now abandoned, and a continuation-in-part of application No. 10/745,757, filed on Dec. 23, 2003, now abandoned.

(60) Provisional application No. 60/459,077, filed on Mar. 31, 2003.

(56) References Cited

U.S. PATENT DOCUMENTS

| | | | | |
|---|---|---|---|---|
| 4,692,147 | A | 9/1987 | Duggan | |
| 4,739,764 | A * | 4/1988 | Lue et al. | 607/40 |
| 4,771,779 | A | 9/1988 | Tanagho et al. | |
| 4,881,526 | A | 11/1989 | Johnson et al. | |
| 4,987,897 | A | 1/1991 | Funke | |
| 4,994,019 | A | 2/1991 | Fernandez et al. | |
| 5,083,908 | A | 1/1992 | Gagnebin et al. | |
| 5,199,428 | A | 4/1993 | Obel et al. | |
| 5,207,218 | A | 5/1993 | Carpentier et al. | |
| 5,300,107 | A | 4/1994 | Stokes et al. | |
| 5,312,453 | A | 5/1994 | Shelton et al. | |
| 5,330,507 | A | 7/1994 | Schwartz | |
| 5,382,236 | A | 1/1995 | Otto et al. | |
| 5,417,719 | A | 5/1995 | Hull et al. | |
| 5,425,751 | A | 6/1995 | Baeten et al. | |
| 5,454,840 | A | 10/1995 | Krakovsky et al. | |
| 5,474,552 | A | 12/1995 | Palti | |
| 5,480,656 | A | 1/1996 | Okada et al. | |
| 5,501,703 | A | 3/1996 | Holsheimer et al. | |
| 5,509,888 | A | 4/1996 | Miller | |
| 5,540,730 | A | 7/1996 | Terry, Jr. et al. | |
| 5,551,849 | A | 9/1996 | Christiansen | |
| 5,609,575 | A | 3/1997 | Larson et al. | |
| 5,639,275 | A | 6/1997 | Baetge et al. | |
| 5,643,330 | A | 7/1997 | Holsheimer et al. | |
| 5,683,432 | A | 11/1997 | Goedeke et al. | |
| 5,707,642 | A | 1/1998 | Yue | |
| 5,733,313 | A | 3/1998 | Barreras, Sr. et al. | |
| 5,800,465 | A | 9/1998 | Thompson et al. | |
| 5,876,425 | A | 3/1999 | Gord et al. | |
| 5,957,958 | A | 9/1999 | Schulman et al. | |
| 5,984,854 | A | 11/1999 | Ishikawa et al. | |
| 6,002,964 | A * | 12/1999 | Feler et al. | 607/46 |
| 6,015,393 | A | 1/2000 | Hovland et al. | |
| 6,055,456 | A * | 4/2000 | Gerber | 607/117 |
| 6,185,452 | B1 | 2/2001 | Schulman et al. | |
| 6,208,894 | B1 | 3/2001 | Schulman et al. | |
| 6,210,368 | B1 | 4/2001 | Rogers | |
| 6,238,423 | B1 | 5/2001 | Bardy | |
| 6,263,246 | B1 | 7/2001 | Goedeke et al. | |
| 6,283,949 | B1 | 9/2001 | Roorda | |
| 6,322,330 | B1 | 11/2001 | Thomas | |
| 6,358,202 | B1 | 3/2002 | Arent | |
| 6,366,814 | B1 | 4/2002 | Boveja et al. | |
| 6,421,566 | B1 | 7/2002 | Holsheimer | |
| 6,449,512 | B1 | 9/2002 | Boveja | |
| 6,458,118 | B1 | 10/2002 | Lent et al. | |
| 6,464,670 | B1 | 10/2002 | Mulholland | |
| 6,471,645 | B1 | 10/2002 | Warkentin et al. | |
| 6,485,464 | B1 | 11/2002 | Christenson et al. | |
| 6,551,290 | B1 | 4/2003 | Elsberry et al. | |
| 6,587,719 | B1 | 7/2003 | Barrett et al. | |
| 6,609,025 | B2 | 8/2003 | Barrett et al. | |
| 6,650,943 | B1 | 11/2003 | Whitehurst et al. | |
| 6,658,297 | B2 | 12/2003 | Loeb | |
| 6,669,663 | B1 | 12/2003 | Thompson | |
| 6,735,474 | B1 | 5/2004 | Loeb et al. | |
| 6,862,479 | B1 | 3/2005 | Whitehurst et al. | |
| 6,885,895 | B1 * | 4/2005 | Whitehurst et al. | 607/39 |
| 6,901,287 | B2 | 5/2005 | Davis et al. | |
| 6,907,293 | B2 | 6/2005 | Grill et al. | |
| 6,941,171 | B2 | 9/2005 | Mann et al. | |
| 6,944,497 | B2 | 9/2005 | Stypulkowski | |
| 7,734,355 | B2 * | 6/2010 | Cohen et al. | 607/118 |
| 2002/0055761 | A1 | 5/2002 | Mann et al. | |
| 2002/0055779 | A1 | 5/2002 | Andrews | |
| 2002/0082665 | A1 | 6/2002 | Haller et al. | |
| 2003/0004533 | A1 | 1/2003 | Dieck et al. | |
| 2003/0004553 | A1 | 1/2003 | Grill et al. | |
| 2003/0045919 | A1 | 3/2003 | Swoyer et al. | |
| 2003/0100930 | A1 | 5/2003 | Cohen et al. | |
| 2003/0236557 | A1 | 12/2003 | Whitehurst et al. | |
| 2004/0049240 | A1 * | 3/2004 | Gerber et al. | 607/40 |
| 2004/0073197 | A1 | 4/2004 | Kim | |
| 2004/0193228 | A1 | 9/2004 | Gerber | |
| 2005/0010259 | A1 | 1/2005 | Gerber | |
| 2005/0010260 | A1 | 1/2005 | Gerber | |
| 2005/0015117 | A1 | 1/2005 | Gerber | |
| 2005/0020970 | A1 | 1/2005 | Gerber | |
| 2005/0021008 | A1 | 1/2005 | Gerber | |
| 2005/0033372 | A1 | 2/2005 | Gerber | |
| 2005/0033373 | A1 | 2/2005 | Gerber | |
| 2005/0033374 | A1 | 2/2005 | Gerber | |
| 2005/0070969 | A1 | 3/2005 | Gerber | |
| 2005/0096709 | A1 | 5/2005 | Skwarek et al. | |
| 2005/0113877 | A1 | 5/2005 | Spinelli et al. | |
| 2005/0113878 | A1 | 5/2005 | Gerber | |
| 2005/0131484 | A1 | 6/2005 | Boveja et al. | |
| 2005/0209652 | A1 | 9/2005 | Whitehurst et al. | |
| 2005/0216069 | A1 | 9/2005 | Cohen et al. | |
| 2005/0228451 | A1 | 10/2005 | Jaax et al. | |
| 2005/0261746 | A1 | 11/2005 | Gross et al. | |
| 2006/0004421 | A1 | 1/2006 | Bennett et al. | |
| 2006/0020297 | A1 | 1/2006 | Gerber et al. | |
| 2006/0095088 | A1 | 5/2006 | De Ridder | |
| 2006/0122659 | A9 | 6/2006 | Gerber | |
| 2006/0149345 | A1 | 7/2006 | Boggs, II et al. | |
| 2006/0173507 | A1 | 8/2006 | Mrva et al. | |
| 2007/0173900 | A1 | 7/2007 | Siegel et al. | |
| 2007/0255333 | A1 | 11/2007 | Giftakis et al. | |

OTHER PUBLICATIONS

Schmidt, Richard A., "Technique of Pudendal Nerve Localization for Block or Stimulation," The Journal of Urology, vol. 142, pp. 1528-1531 (Dec. 1989).

Medtronic Instruction for Use Manual, "Interstim® Therapy," Model 3080, 3092, 3886 and 3966 (32 pages) Jul. 18, 2005.

Medtronic Instruction for Use Manual, "Interstim®," Model 3080, 3092, 3886 and 3966 (36 pages) Oct. 24, 2005.

Medtronic Instruction for Use Manual, "Pisces Quad®, Compact® and Pisces Quad Plus®," Model 3487A, 3887 and 3888 (16 pages) Jan. 22, 2004.

Medtronic Instruction for Use Manual, "Interstim®," Model 4350 (40 pages) 2005.

Medtronic Instruction for Use Manual, "Interstim® Therapy," Model 3058 and 3023 (32 pages) May 5, 2006.

Medtronic Instruction for Use Manual, "Itrel® 3," Model 7425 (78 pages) Jul. 12, 2005.

Medtronic Instruction for Use Manual, "Synergy™ and Synergy Versitrel™," Model 7427 and 7427V (96 pages) Oct. 30, 2003.

Medtronic Instruction for Use Manual, Model 7424 (57 pages) Sep. 1993.

U.S. Appl. No. 09/713,598, filed Nov. 15, 2000, entitled "Minimally Invasive Apparatus for Implanting a Sacral Stimulation Lead."

Chalfin, S.A., "Neural Stimulation as a Method of Controlling Prostatitis Symptoms," disclosed in 1999 Selected Abstracts from American Urological Association Annual Meeting, 2 pages.

Office Action dated Nov. 26, 2010 for U.S. Appl. No. 11/414,509, (8 pgs.).

Request for Continued Examination (RCE) and Amendment dated Feb. 28, 2011 for U.S. Appl. No. 11/414,509 (18 pgs.).

Murovic, J. A., Kim, D. H., Tiel, R. L., Kline, D. G., "Surgical Management of 10 Genitofemoral Neuralgias at the Louisiana State University Health Sciences Center," Neurosurgery, vol. 56, No. 2, pp. 298-303, www.neurosurgery-online.com, Feb. 2005.

(56) References Cited

OTHER PUBLICATIONS

Kim, D. H., Murovic, J. A., Tiel, R. L., Kline, D. G., "Surgical Management of 33 Ilioinguinal and Iliohypogastric Neuralgias at the Louisiana State University Health Sciences Center," Neurosurgery, vol. 56, No. 5, pp. 1013-1020, , www.neurosurgery-online.com, May 2005.

Brindley, G. S., "Sacral root and hypogastric plexus stimulators and what these models tell us about autonomic actions on the bladder and urethra," Clinical Science, vol. 70 (Suppl. 14), pp. 41s-44s, 1986.

Granitsiotis, P., Kirk, D.; "Chronic Testicular Pain: An Overview," European Urology, vol. 45, pp. 430-436, 2004.

Sasaoka, N., Kawaguchi, M., Yoshitani, K., Kato, H., Suzuki, A., Furuya, H., "Evaluation of genitofemoral nerve block, in addition to ilioinguinal and iliohypogastric nerve block, during inguinal hernia repair in children", British Journal of Anaesthesia, vol. 94 No. 2, pp. 243-246, 2005.

Berman, J., Berman, L., "Female Sexual Function and Dysfunction", Annual Meeting of American Urological Association, Inc., May 29, 2002, 33 pages.

Yucel, S., Baskin, L. S., "The neuroanatomy of the human scrotum:surgical ramifications", BJU International, vol. 51, pp. 393-397, 2003.

Levine, L. A., Matkov, T. G., "Microsurgical Denervation of the Spermatic Cord as Primary Surgical Treatment of Chronic Orchialgia", The Journal of Urology, vol. 165, pp. 1927-1929, Jun. 2001.

Gillitzer, R., Hampel, C., Wiesner, C., Pahernik, S., Melchior, S., Thuroff, J. W., "Pudendal Nerve Branch Injury During Radical Perineal Prostatectomy," Journal of Urology, vol. 67, No. 2, 2006, (3 pages).

Uchio, E. M., Yang, C. C., Kromm, B. G., Bradley, W. E., "Cortical Evoked Responses from the Perineal Nerve," The Journal of Urology, vol. 162, pp. 1983-1986, Dec. 1999.

The Pain Clinic, "Peripheral Nerve Blocks", http://www.painclinic.org/treatment-peripheralnerveblocks.htm, 2006, (11 pages).

Mayo Foundation for Medical Education and Research, "Urinary Incontinence", http://www.mayoclinic.com/health/urinaryincontinence/DS00404/DSECTION=8, 2006, (5 pages ).

Mayo Foundation for Medical Education and Research, "Erectile Dysfunction", http://www.mayoclinic.com/health/erectiledysfunction/DS00162/DSECTION=7, Jan. 18, 2006, (3 pages).

New York School of Regional Anesthesia, "Genitofemoral Block", http://www.nysora.com/techniques/genitofemoral_block/, 2006, (3 pages).

Hruby et al., "Anatomy of pudendal nerve at urogenital diaphragm—new critical site for nerve entrapment", Journal of Urology, vol. 66, Issue 5, Nov. 2005, pp. 949-952.

Bolandard et al., European Society of Regional Anaesthesia and Pain Therapy, "Ilioinguinal-Iliohypogastric Block—Single Shot", 2006, (2 pages).

Lamer et al., "Treatment of Iliohypogastric Neuralgia with Subcutaneous Peripheral Nerve Stimulation," Poster Abstract Form, 9th Annual Meeting, North American Neuromodulation Society, Nov. 10-12, 2005 (1 pg.).

Restriction Requirement dated Feb. 8, 2010 for U.S. Appl. No. 11/414,509, (7 pgs.).

Response to Restriction Requirement dated Mar. 10, 2010 for U.S. Appl. No. 11/414,509, (2 pgs.).

Office Action dated Jun. 14, 2010 for U.S. Appl. No. 11/414,509, (11 pgs.).

Responsive Amendment dated Sep. 14, 2010 for U.S. Appl. No. 11/414,509, (15 pgs.).

Office Action from U.S. Appl. No. 11/414,509, dated Mar. 15, 2013, 11 pp.

\* cited by examiner

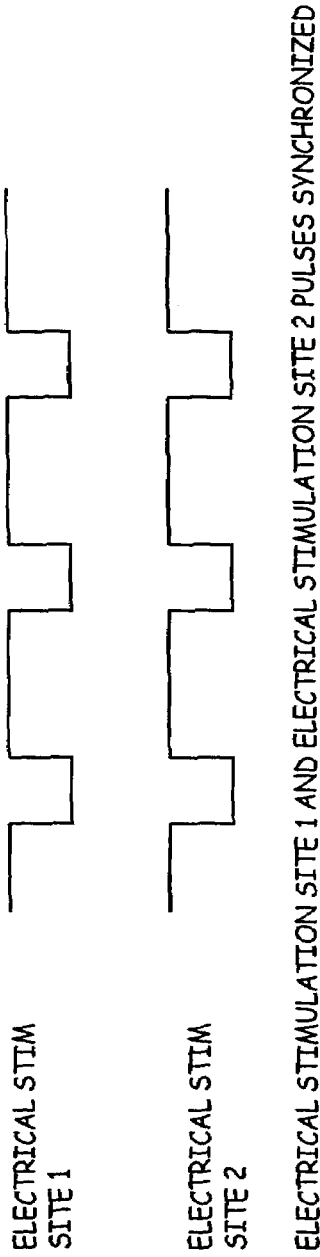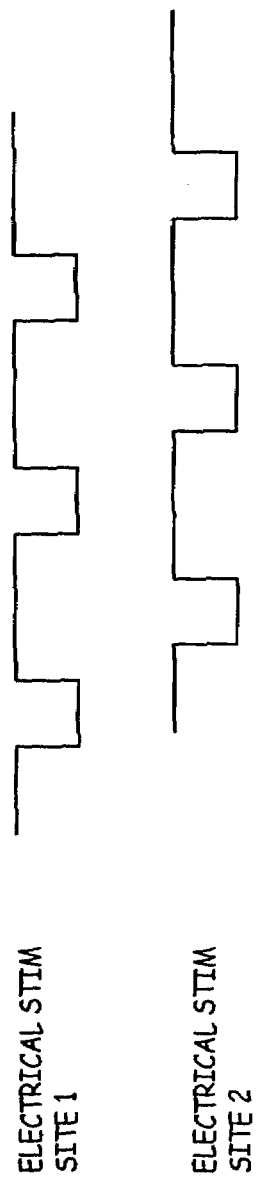

ELECTRICAL STIMULATION AT SITE 1 AND ELECTRICAL STIMULATION AT SITE 2 WITH ELECTRICAL STIMULATION AT SITE 2 TURNED OFF FOR A PERIOD OF TIME.

ELECTRICAL STIMULATION AT SITE 1 AND ELECTRICAL STIMULATION AT SITE 2 WITH SITE 1 AND SITE 2 STIMULATION TURNED OFF AFTER A PERIOD OF TIME.

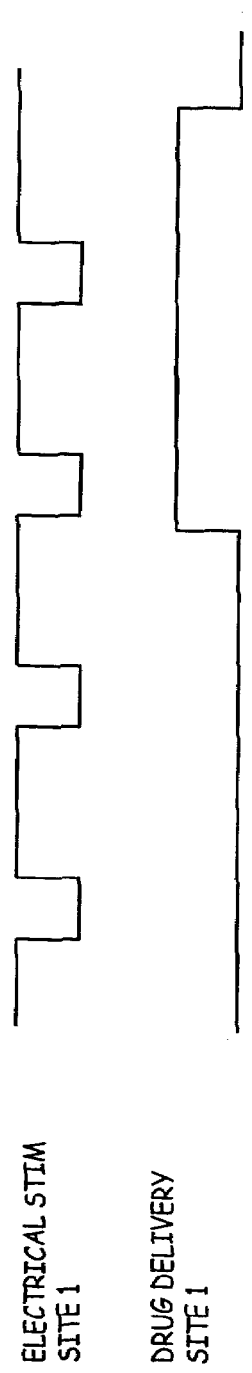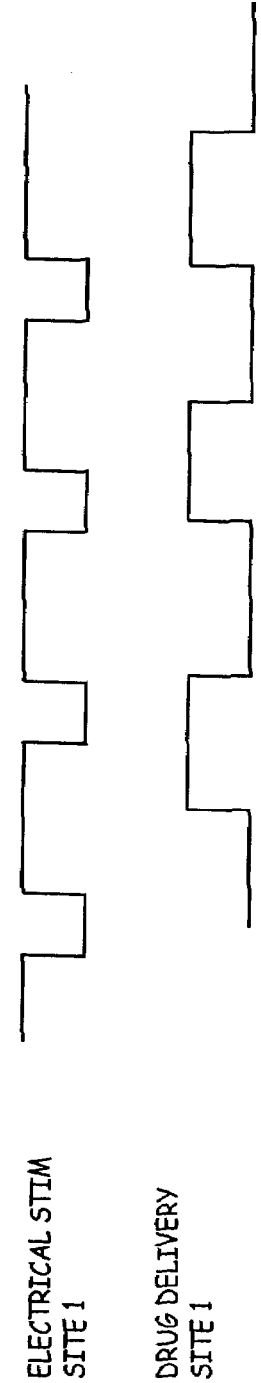

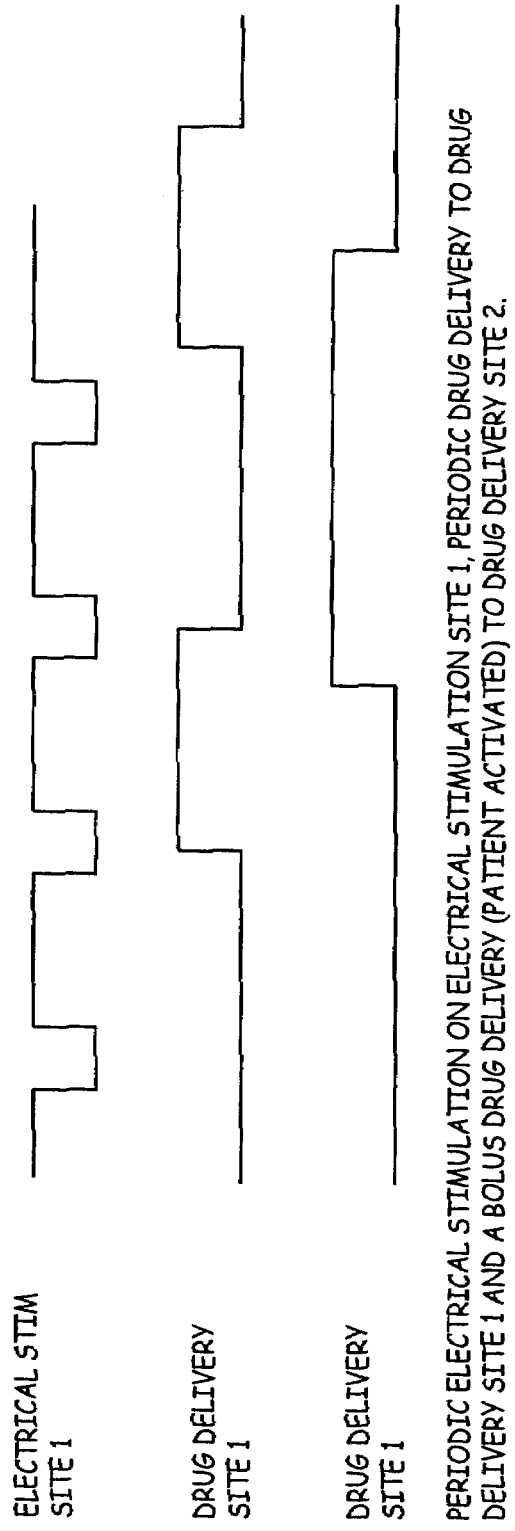

PERIODIC DRUG DELIVERY TO DRUG DELIVERY SITE 1.

CONTINUOUS DRUG DELIVERY TO DRUG DELIVERY SITE 1.

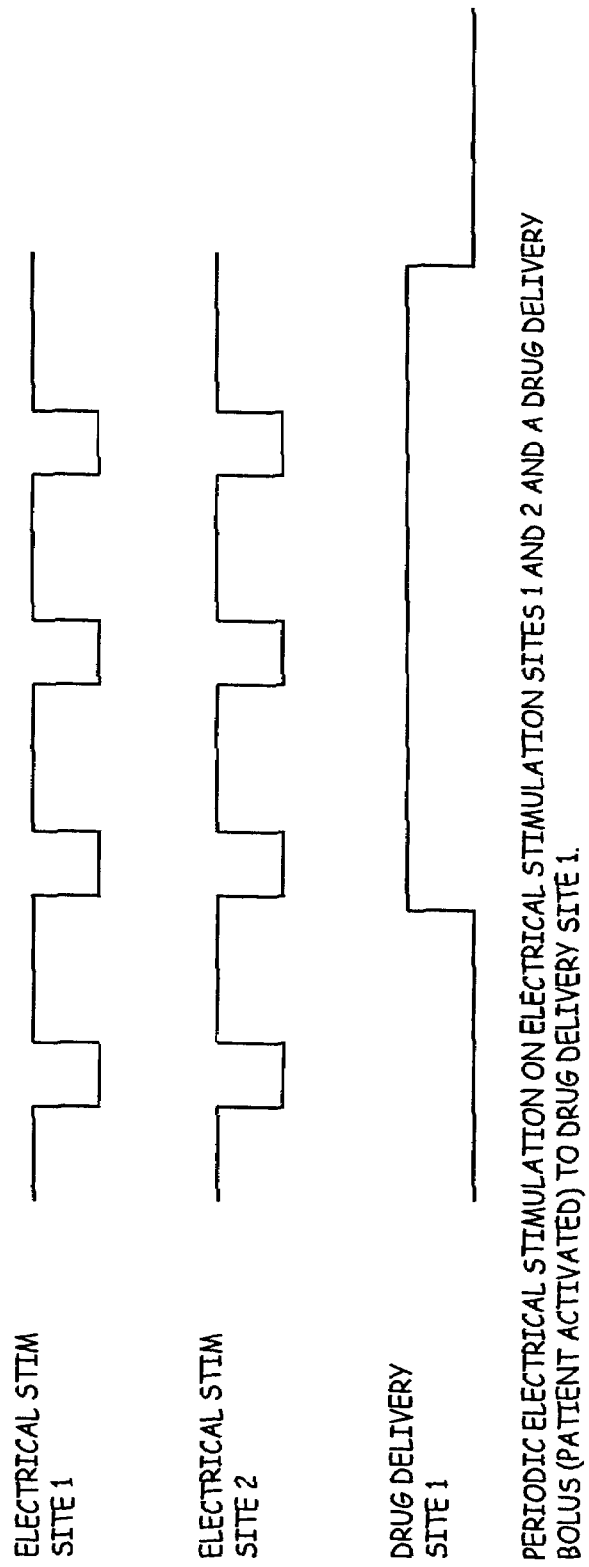

METHOD, SYSTEM AND DEVICE FOR TREATING DISORDERS OF THE PELVIC FLOOR BY ELECTRICAL STIMULATION OF THE SACRAL AND/OR PUDENDAL NERVES

This application is a continuation of U.S. patent application Ser. No. 10/836,924, filed Apr. 30, 2004, which is incorporated herein by reference in its entirety.

U.S. patent application Ser. No. 10/836,924 is a continuation-in-part of each of the following U.S. Patent Applications: (1) U.S. patent application Ser. No. 10/236,578 to Gerber et al. entitled "Electrical and/or Magnetic Stimulation Therapy for the Treatment of Prostatitis and Prostatodynia" filed Sep. 6, 2002; (2) U.S. patent application Ser. No. 10/723,316 to Spinelli et al. entitled "Method, System and Device for Treating Disorders of the Pelvic Floor by Means of Electrical Stimulation of the Pudendal Nerves and Associated Nerves, and the Optional Delivery of Drugs in Association Therewith" filed Nov. 26, 2003, which issued as U.S. Pat. No. 7,328,068 on Feb. 5, 2008, and which claims the benefit of U.S. Provisional Application No. 60/459,077 also to Spinelli et al. and having the same title filed Mar. 31, 2003; (3) U.S. patent application Ser. No. 10/723,903 to Gerber entitled "Method, System and Device for Treating Various Disorders of the Pelvic Floor by Electrical Stimulation of the Pudendal Nerves and the Sacral Nerves at Different Sites" filed Nov. 26, 2003; and (4) U.S. patent application Ser. No. 10/745,757 to Gerber entitled "Method, System and Device for Treating Various Disorders of the Pelvic Floor by Electrical Stimulation of the Left and Right Pudendal Nerves" filed Dec. 23, 2003. This application hereby incorporates by reference herein the foregoing '578, '316, '903 and '757 patent applications, and the '077 provisional application, each in its respective entirety.

FIELD OF THE INVENTION

This invention relates to methods, systems and devices for treating various disorders of the pelvic floor by delivering electrical stimuli.

BACKGROUND

The medical device industry produces a wide variety of electronic and mechanical devices for treating patient medical conditions. Depending upon the medical condition, medical devices may be surgically implanted or connected externally to a patient receiving treatment. Clinicians use medical devices alone or in combination with drug therapies and surgery to treat patient medical conditions. For some medical conditions, medical devices provide the best (and sometimes the only) therapy to restore an individual to a more healthful condition and a fuller life. Conditions that medical devices may effectively treat include pelvic floor disorders.

Pelvic floor disorders adversely affect the health and quality of life of millions of people. Pelvic floor disorders include urinary control disorders such as urge incontinency, urge frequency, voiding efficiency, fecal control disorders, sexual dysfunction, and pelvic pain. Individuals with urinary control disorders often face debilitating challenges in their everyday lives. These individuals may be preoccupied with trips to the bathroom, fears of embarrassment and sleepless nights. Some suffers become so anxious that they become isolated and depressed. Pelvic floor disorders may be treated with a variety of therapeutic options such as behavior modification including biofeedback, pharmacological treatment, mechanical intervention such as self-catheterization, physical appliances such as diapers, and surgical intervention. Surgical treatments are the most invasive and are often considered after other therapies have proven ineffective.

Urinary incontinence, or the inability to control the passage of urine, is a relatively common problem. Although there are a variety of different types of urinary incontinence, stress incontinence, urge incontinence and urinary retention are the most common.

Stress incontinence is the unacceptable passage of urine under the stress of increased abdominal pressure. This increased pressure typically results from coughing, sneezing, and Valsalva. Stress incontinence is manifested urologically by normal cystometry, obtuse urethral vesicular angle, abnormally low urethral pressures and a physiologically short urethral length. This disorder is most common in multiparous, post-menopausal females. Physiologically, stress incontinence is a disorder of the volitional muscular control of the urethral resistance to the flow of urine. Laxity and partial denervation of the pelvic musculature is the chief abnormality.

Urge incontinence is the involuntary passage of urine with a concomitant sense of urgency. Systometry indicates detrusor (bladder wall muscle) contractions with low bladder filling pressures and volumes. These bladder contractions may not be inhibited in the presence of voluntary EMG signals from the sphincter, indicating reduction or loss of the pudendal-parasympathetic inhibitory reflex. Unsolicited, premature bladder contraction may result from mucosal irritation of varied etiology. These premature contractions of the bladder may also be the result of an abnormally high gain in the detrusor contractile reflex due to the loss of inhibitory control with an upper-motor-neuron lesion.

Urinary retention is characterized by the inability of a patient to spontaneously and controllably urinate or void. Catheterization of the urethra is provided to many patients suffering from urinary retention, which is often a painful and somewhat lengthy procedure having the added risk of causing infection.

Constipation is a life-disturbing problem that afflicts millions of Americans, from the very young to the elderly. Although relatively rare among the young, it is a very common problem in middle age, and is a nearly ubiquitous problem in the elderly. Chronic constipation is a major problem for many individuals, and frequently causes extreme discomfort to the afflicted. Such discomfort may be a major obstacle to leading a normal life, and may consume an enormous amount of the afflicted person's energy and time.

Besides causing severe discomfort, chronic constipation may also be harmful to the patient. For example, chronic constipation may result in an intestinal obstruction that may cause the patient great pain; or that may even cause the patient's death, unless surgically corrected. Chronic constipation may also prevent the patient from receiving the benefit of certain needed prescription medications, because the medications may have undesirable side effects on an already constipated gut.

Conventional therapies for chronic constipation are often distasteful and unpleasant at best, since they may involve treatments such as repeated consumption of large quantities of laxatives, repetitive use of enemas, or both. Repeatedly consuming large quantities of laxatives may be harmful to the patient, since they may result in dehydration or even renal failure. The repetitive use of enemas may be harmful since they may irritate or physically harm the treated portion of the patient's gut.

Chronic constipation is usually thought of in association with problems of the large intestine. Other parts of the patient's gut, however, may also exhibit chronic constipation-like problems, such as the esophagus, the stomach, and less frequently, the small intestine. Problems associated with chronic constipation may include depressed motility of the esophagus, stomach or small intestine. For simplicity, chronic constipation, or chronic constipation-like problems, of any portion of the patient's gut from the esophagus to the anus will be referred to hereafter as simply "constipation".

The prostate is a glandular and fibromuscular organ in the male, which lies immediately below the bladder and surrounds the urethra. Prostatitis, the third leading disease of the prostate, is a common urologic condition that many clinicians find difficult to treat effectively.

The main symptom of chronic prostatitis (category III) is pain, followed by variable voiding (urgency/frequency) and erectile or sexual dysfunction. Patients have symptoms such as painful ejaculation or pain in the penis, testicles, or scrotum; low back, rectal or perineal pain; pain along the inner aspects of the thighs; irritative or obstructive urinary symptoms; and decreased libido or impotence. As a rule, chronic non-bacterial prostatitis patients do not have recurrent urinary tract infections.

Chronic prostatitis is a major male health issue. The average urologist in the U.S. sees 173 prostatitis patients per year, of which one-third are newly diagnosed. The prevalence of prostatitis in the general male population is estimated to be 5-8.8%, and it has been estimated that about 2 million office visits per year are related to prostatitis. Self-reported histories of prostatitis are as prevalent as 16% of all reported cases. Patients with chronic prostatitis experience a negative impact on quality of life comparable to patients with unstable angina, recent myocardial infarction or active Crohn's disease. The average age of the prostatitis population is estimated at 50 years. Prostatitis is the most common urologic diagnosis in men under 50 years old and the third most common in men over 50 years old. The most common classification of prostatitis is chronic prostatitis/chronic pelvic pain syndrome (category III), which may include as many as 90% of all patients who meet the criteria of the condition.

Despite the widespread prevalence of prostatitis, the diagnosis of chronic prostatitis represents a particular challenge since its diagnosis is often based on exclusion. Prostatitis remains poorly understood despite its prevalence because it encompasses multiple diverse disorders that cause symptoms related to the prostate gland. The etiology of acute and chronic bacterial prostatitis is clearly defined, and is a result of pathogenic bacteria that may cause systemic symptoms or urinary tract infections. On the other hand, chronic prostatitis/chronic pelvic pain syndrome does not have a clearly defined etiology, and there are many theories about the cause of this disease.

Perhaps the most comprehensive or encompassing theory of chronic non-bacterial prostatitis is one which advocates a multifactorial mechanism initiated by a stimulus such as infection or trauma. An interrelated cascade of events may follow, including physical, chemical, immunologic or neurogenic components, resulting in a local response of inflammation and/or neurogenic injury.

In the absence of consistent or clear etiologies for chronic prostatitis/chronic pelvic pain syndrome, improvement in quality of life and a reduction in symptoms are the usual goals of therapy. The most common treatment for chronic prostatitis involves pharmacologic treatments such as antibiotics, anti-inflammatory agents, alpha blockers, anti-spasmodics, analgesics, allopurinol, and muscle relaxants. Alpha blockers have successfully treated symptoms of prostatitis, although adverse event rates have been high. Muscle relaxants have shown significant improvement in small studies for category IIIB patients with sphincter dyssynergia or muscle spasm. Anti-inflammatory agents, such as pentosan polysulfate, have proven successful for approximately 40% of patients with category IIIA prostatitis.

Phytotherapeutic agents have demonstrated improvements in small studies for pain and irritative voiding. Other treatments include physiotherapy (such as biofeedback and pelvic muscle exercises) and various modalities of invasive and minimally invasive procedures (e.g., transurethral microwave therapy, transurethral incision of the bladder neck, hydrodistensions, acupuncture, electroneuromodulation, balloon dilation, YAG laser therapy and heat therapy). Repetitive prostatic massage is a popular treatment method due to the failure of consistent standard medical therapy to treat the condition. Lifestyle changes, such as meditation, discontinuation of bike riding, sitz-baths, dietary changes and chiropractic therapy, are often prescribed.

As a result of unknown etiology, unsure diagnosis and treatment options that are often myriad and ineffective, chronic prostatitis is a "diagnosis of exclusion" and has a poor record of treatment success. Accordingly, the present invention is intended to provide solutions to the foregoing problems through improved and more effective methods of treating pain and other symptoms associated with chronic prostatitis, prostatalgia and prostatodynia.

Sexual dysfunction comprises a broad range of maladies, including erectile dysfunction, orgasmic dysfunction, premature ejaculation and lack of lubrication. Sexual dysfunctions plague both women and men, and may be life-long or acquired. To treat impotence (also called erectile dysfunction), electrical conductors may be implanted near the surface of the pelvic splanchnic nerve. Stimulation of this nerve with low voltage electrical pulses is believed to cause arterioles dilation and initiate erection. Also, it is known that implantation of an electrode on the cavernous nerves of a male, adjacent to his prostate gland, may also cause penile erection. Further, other electrical impulse devices exist that are not implanted but instead apply electrical stimuli topically to the coccyx region to promote sexual excitation. Impotence, however, should not be confused with orgasmic dysfunction, where satisfactory erection may be obtained but there is an absence of orgasm.

Current treatment of orgasmic dysfunction concentrates on the psychological components of the disorder rather than the physiological components. Orgasmic dysfunction is a physical malady that results in marked distress and interpersonal difficulty. The physical disorder causes psychological performance anxiety and pressure. Sexual desire and frequency usually decline. The patient's intimate relationships usually suffer from resentment and conflict. There is anecdotal evidence of patients who have experienced mild sensations in the genitalia while undergoing spinal cord stimulation for pain relief.

Spinal cord stimulation, on the other hand, has been used as a treatment for chronic painful conditions for approximately thirty years. Commonly, spinal cord stimulation is used to alleviate pain after failed surgery, pain due to neuropathies, or pain due to inadequate blood flow. Neurostimulation systems have been found to relieve chronic, intractable pain in the limbs or trunk.

The basic concept of neurostimulation as it relates to pain relief involves the substitution of sensations that reach the thalamus of the brain. Rather than a pain message, the spinal cord stimulation closes the gate in the spinal cord and replaces the pain sensation with a tingling sensation. Electrodes are positioned effectively to create paresthesia in the painful area.

Paresthesia refers to a change in sensation in an area of the body. Usually paresthesia is used to show change in neurologic function caused by damage to a nerve or nerves. Paresthesia is usually not an absence of sensation, but a decrease or alteration of sensation. Patients have described paresthesia as a "buzzing sensation."

Paresthesia is accomplished through the implantation of stimulating electrodes within or near the spinal cord. The electrodes are inserted between the vertebrae in parallel with the spinal cord. Low-voltage electrical stimulation is precisely applied to the spinal cord. Through direct stimulation of the dorsal column or the targeted peripheral nerve, the sensation of pain is replaced by a more pleasant "tingling" sensation. The sensation may be adjusted in terms of amplitude to control intensity and pulse width to control duration and frequency. Usually such neurostimulation systems are implantable. Medtronic Neurological, a division of Medtronic, Inc. of Minneapolis, Minn., sells a neurostimulator system used for pain relief. The device has been approved by the Federal Drug Administration for implantation in the spinal cord to alleviate pain.

One surgical technique to treat urinary control disorders is the implantable InterStim® therapy, available from Medtronic, Inc., which applies mild electrical stimulation to the sacral nerves in the lower region of the spine to influence the behavior of structures such as the bladder, sphincter and pelvic floor muscles. Generally, implantation of the InterStim system involves surgically implanting a stimulation lead near the sacral nerves. The stimulation lead is a very small, insulated, electrical conductor with electrical stimulation contacts on the distal end for implantation near the sacral nerves and an electrical connector on the proximal end of the lead. The lead electrical connector is typically connected to a small extension, and the extension is connected to a small neurostimulator that operates in a fashion broadly similar to that of a cardiac pacemaker by delivering occasional small electrical pulses that sometimes create a tingling sensation felt by the patient. The stimulation lead, lead extension and neurostimulator are all implanted in the patient in a manner that is typically not perceptible by others. InterStim therapy may improve the condition of a pelvic floor disorder patient and allow the patient to lead a full life. InterStim therapy is also nondestructive and reversible.

Each year thousands of patients have sacral nerve stimulation systems implanted within them for the treatment of urinary incontinence and urinary retention. Therapy success is determined through the evaluation of symptoms related to the disorder. Clinical success for most therapies, including sacral nerve stimulation, is defined as a 50% decrease in the following symptoms:

Urge incontinence as measured by:
Average number of incontinent episodes per day, or
Average severity ranking of incontinent episodes, or
Average number of absorbent pads or diapers replaced due to incontinence.
Urinary frequency and urgency as measured by:
Average number of voids per day, or
Average voided volume per void, or
Average degree of urgency prior to voiding.
Urinary retention as measured by:
Decrease in post-void urine residual, or
Average number of catheterizations consisting of ≥100 ml of urine, or
Average catheter volume per catheterization (post-void residual).

Today, electrical stimulation of the sacral nerve is fairly common for the purpose of treating voiding dysfunction. Although the majority of patients receiving sacral nerve stimulation obtain satisfactory relief of their voiding dysfunction, some patients (less than 50%) do not experience adequate relief from sacral nerve stimulation techniques or desire to obtain better results from the therapy.

Electrical stimulation delivered by an intravaginal or a perineal surface electrode has been shown to inhibit premature and inappropriate detrusor contractions. The mechanism for such effects appears to derive from the electrical stimulation of pudendal nerve afferents (sensory receptors or sensory nerve fibers). Input into the pudendal afferent system inhibits a parasympathetic reflex loop consisting of bladder wall afferents (sensory reflexes) and efferents (motor reflexes). This parasympathetic loop normally senses a distension of the bladder via the afferent limb and responds by sending an efferent signal to contract the bladder. Although such stimulation has shown therapeutic effects, electrode placement and on-going stimulation do not lend themselves easily to chronic stimulation.

Stimulation of the pudendal nerve as an alternative to sacral nerve stimulation has been proposed in past. The invasiveness of the surgical procedure for implanting electrical stimulation leads and other reasons have made stimulation of the pudendal nerve impractical, however. Since the pudendal nerve directly innervates much of the pelvic floor, it is believed to be a more optimal stimulation site with few undesired side effects. Advancements in minimally invasive lead placement techniques along with advancement in lead anchoring techniques have resulted in the increased viability of chronic stimulation of the pudendal nerve.

Some prior art publications relating to various embodiments of the present invention are listed in Table 1 below.

TABLE 1

| Prior Art Publications |
| --- |
| Juenemann et al., "Clinical Significance of Sacral and Pudendal Nerve Anatomy," The Journal of Urology, Vol. 139, pp. 74-80 (January, 1988). |
| Schmidt, Richard A., "Technique of Pudendal Nerve Localization for Block or Stimulation," The Journal of Urology, Vol. 142 (December, 1989). |
| U.S. Pat. No. 4,406,288 to Cash for "Bladder Control Device and Method." |
| U.S. Pat. No. 4,607,639 to Tanagho et al. for "Method and System for Controlling Bladder Evacuation." |
| U.S. Pat. No. 4,771,779 to Tanagho et al. for "System for Controlling Bladder Evacuation." |
| U.S. Pat. No. 4,739,764 to Lue et al. for "Method for Stimulating Pelvic Floor Muscles for Regulating Pelvic Viscera." |
| U.S. Pat. No. 4,881,526 to Johnson et al. for "Intravaginal Electrode and Stimulation System for Controlling Female Urinary Incontinence." |
| U.S. Pat. No. 5,425,751 to Baeten et al. for "Method and Apparatus for Optimum Positioning of a Muscle Stimulating Implant." |

TABLE 1-continued

Prior Art Publications

U.S. Pat. No. 5,540,730 to Terry, Jr. et al. for "Treatment of Motility Disorders by Nerve Stimulation."
U.S. Pat. No. 5,984,854 to Ishikawa et al. for "Method for Treating Urinary Incontinence and Apparatus Therefore."
U.S. Pat. No. 6,055,456 to Gerber for "Single and Multi-Polar Implantable Lead for Sacral Nerve Stimulation."
U.S. Pat. No. 6,366,814 to Boveja for "Electrical Stimulation Adjunct (Add-On) Therapy for Urinary Incontinence and Urological Disorders Using an External Stimulator."
U.S. Pat. No. 6,449,512 to Boveja for "Apparatus and Method for Treatment of Urological Disorders Using Programmerless Implantable Pulse Generator System."
U.S. Pat. No. 6,587,719 to Barrett et al. for "Treatment of Obesity by Bilateral Vagus Nerve Stimulation."
U.S. Pat. No. 6,609,025 to Barrett et al. for "Treatment of Obesity by Bilateral Sub-Diaphragmatic Nerve Stimulation."
U.S. Pat. No. patent application Publication No. 2002/0055761 to Mann et al. for "Implantable Stimulator Systems and Methods for Treatment of Incontinence and Pain."
U.S. Pat. No. patent application Publication No. 2002/0055779 to Andrews for "Neural Prosthesis."
PCT patent application WO 02/078592 to Grill et al. for "Systems and Methods for Selectively Stimulating Components In, On or Near the Pudendal Nerve or Its Branches to Achieve Selective Physiologic Responses."
European patent application No. 0 245 547 to Tanagho et al. for "Electronic Control System for Controlling Pelvic Viscera via Neuro-Electrical Stimulation."

All patents and technical papers listed in Table 1 hereinabove are hereby incorporated by reference herein, each in its respective entirety. As those of ordinary skill in the art will appreciate readily upon reading the Summary of the Invention, Detailed Description of the Preferred Embodiments and Claims set forth below, at least some of the devices and methods disclosed in the patents and publications of Table 1 may be modified advantageously in accordance with the teachings of the present invention. The foregoing and other objects, features and advantages, which will now become more readily apparent by referring to the following specification, drawings and claims, are provided by the various embodiments of the present invention.

SUMMARY OF THE INVENTION

Simultaneous, concurrent or sequential electrical stimulation of tissue volumes at two or more locations adjacent sacral nerves or nerve portions and/or the pudendal nerve or nerve portions has been discovered to provide a means of more directly or effectively treating various pelvic floor disorders than has been possible heretofore through means of employing conventional therapeutic techniques. Various combinations and permutations of sacral nerve or nerve portion and/or pudendal nerve or nerve portion electrical stimulation provide particularly efficacious means of delivering therapies for a number of different pelvic floor disorders. For example, electrical stimulation of both a left and a right sacral nerve or nerve portion, both a left and a right pudendal nerve or nerve portion, or both a sacral nerve or nerve portion and a pudendal nerve or nerve portion, may provide efficacious therapy for a number of different pelvic floor disorders.

It has been discovered that electrical stimulation of tissue volumes at two or more such locations provides beneficial effects and therapies for various disorders of the pelvic floor over a wider anatomical region than merely electrically stimulating the pudendal or sacral nerves or portions thereof at a single location, or than may be attained through conventional sacral nerve stimulation. Because the present invention provides for more targeted electrical stimulation of the pelvic floor or portions thereof, at least some of the undesirable side effects of sacral nerve stimulation may be avoided or minimized.

Two or more electrical stimulation signals are applied to appropriate portions of a patient's pelvic floor and the sacral and/or pudendal nerves or nerve portions in an amount and manner effective to treat a number of disorders, including, but not limited to, urinary and/or fecal voiding dysfunctions such as constipation, incontinence disorders such as urge frequency and urinary retention disorders, sexual dysfunctions such as orgasmic and erectile dysfunction, pelvic pain, prostatitis, prostatalgia and prostatodynia. Electrical stimulation parameters and drug type and dosage are tailored to deliver the most efficacious therapy for a given malady.

The two electrical stimulation signals are applied by one or more IMDs that each have at least one medical electrical lead positionable, secured or attached to or in a patient's pelvic floor and in proximity to a sacral nerve or nerve portion or a pudendal nerve or nerve portion. Each such lead carries at least one electrode, and preferably at least two electrodes, positionable or attachable for contact with or in proximity to the patient's sacral nerves or nerve portions or pudendal nerve or nerve portions.

Various embodiments of the present invention are capable of providing one or more solutions to one or more problems existing in the prior art respecting conventional treatment for urinary and/or fecal voiding dysfunctions such as constipation, incontinence disorders such as urge frequency and urinary retention disorders, sexual dysfunctions such as orgasmic and erectile dysfunction, pelvic pain, prostatitis, prostatalgia and prostatodynia.

Such problems include, but are not limited to, one or more of: (a) sequelae or side-effects resulting from the oral administration of pharmaceutical products; (b) the requirement to purchase expensive pharmaceutical products on an on-going basis; (c) not having the ability to terminate or change instantaneously administration of pharmaceutical therapy; (d) not having the ability to target with a great deal of precision or specificity the ailment in question using orally delivered pharmaceutical products; (e) in the case of electrical stimulation, not having a well-defined or reliable method of determining stimulation electrode placement; (f) patients having chronic and essentially untreatable pain having no effective pain relief therapy available for use; (g) patients having to wear diapers, pads or other devices for containing human waste; and/or (h) conventional sacral nerve stimulation techniques being incapable of providing the desired relief or therapy in many patients.

Various embodiments of the present invention are capable of providing one or more advantages, which may include, but are not necessarily limited to: (a) targeting the delivery of therapies with a high degree of specificity; (b) having the ability to change the therapy delivered on-demand or instantaneously; (c) lowering medical care costs in respect of pharmaceutical products; (d) having the potential to delivery superior therapy; (e) permitting stimulation lead implantation surgical procedures to be completed more quickly; (f) reducing trauma or damage to a patient's pelvic floor anatomy; and/or (g) improved physical and electrical coupling of one or more stimulation electrodes to a pertinent sacral nerve or nerve portion.

BRIEF DESCRIPTION OF DRAWINGS

These and other features and advantages of the present invention will be more readily understood by referring to the following detailed description of the preferred embodiments thereof, when considered in conjunction with the drawings, in which like reference numerals indicate identical structures throughout the several views when appropriate. Note that the drawings are not necessarily to scale.

FIGS. 10A through 10F show various embodiments of first and second electrical stimulation pulse regimes of the present invention.

FIGS. 11A through 11G show various embodiments of first and second electrical stimulation pulse regimes and first and second drug delivery regimes of the present invention.

DETAILED DESCRIPTIONS OF THE PREFERRED EMBODIMENTS

Figure 1:
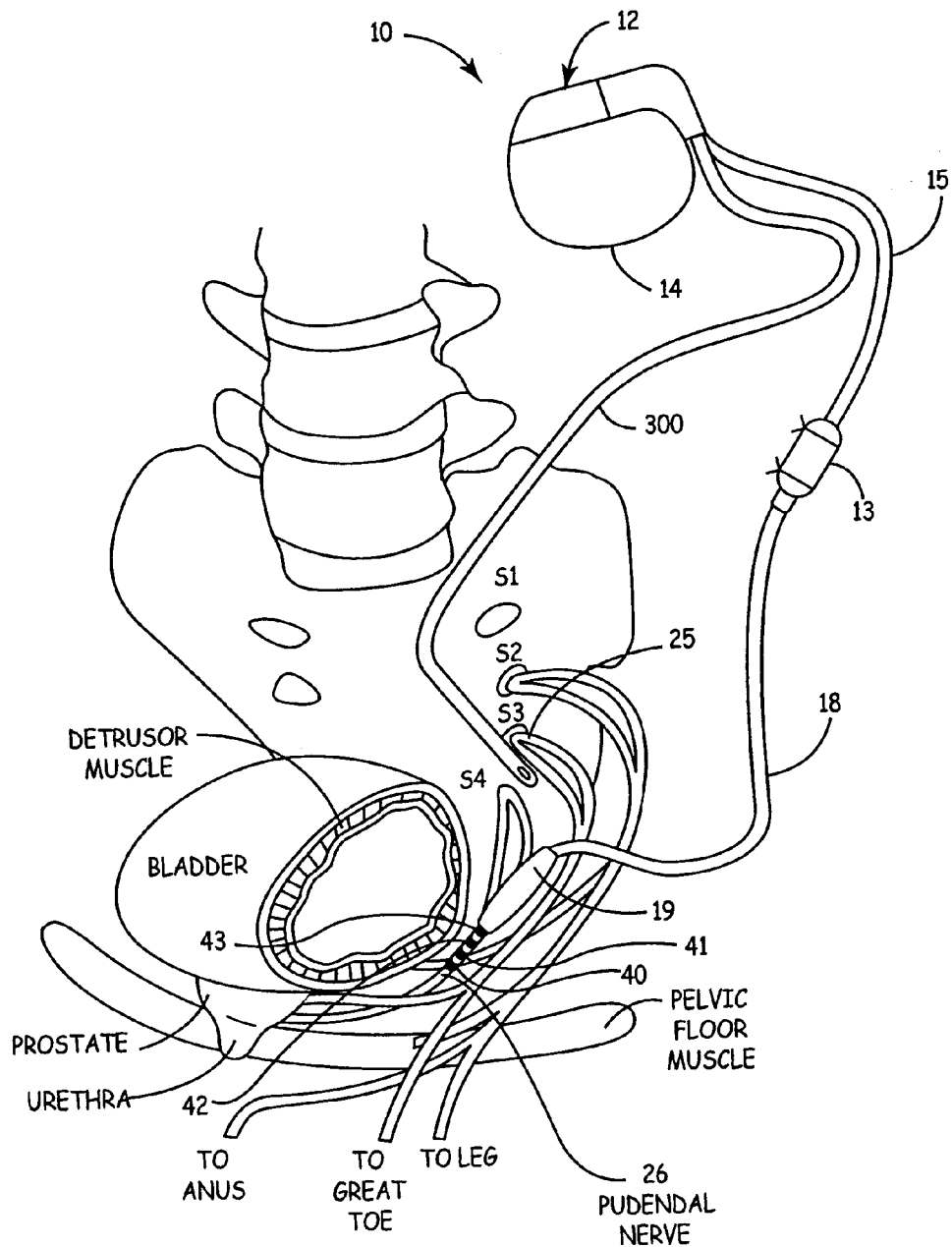
FIG. 1 shows one embodiment of the present invention, where INS 10 is a combination implantable pulse generator and drug pump implanted in an upper buttock position in a patient, lead 18 is implanted near or adjacent to pudendal nerve or nerve portion 26, and drug delivery catheter 300 is implanted near or adjacent to sacral nerve or nerve portion 25, to thereby effect therapeutic relief.

In the following description of the preferred embodiments, reference is made to the accompanying drawings that form a part hereof, and in which are shown by way of illustration several specific embodiments of the invention. It is to be understood that other embodiments of the present invention are contemplated and may be made without departing from the scope or spirit of the present invention. The following detailed description, therefore, is not to be taken in a limiting sense. Instead, the scope of the present invention is to be defined in accordance with the appended claims. As employed herein, the term "sacral nerve 25" means any one of the sacral nerves, portions of the sacral nerve(s), nerves neurologically connected to any one of the sacral nerves and in relatively close physical proximity thereto, and extensions or branches of any one of the sacral nerves. As employed herein, the term "pudendal nerve 26" means the pudendal nerve itself, portions of the pudendal nerve, nerves neurologically connected to the pudendal nerve and in relatively close physical proximity thereto, and extensions or branches of the pudendal nerve. Additionally, the term "INS 10" as employed herein is not necessarily limited to meaning an "implantable neurological stimulator" only, but may also mean, depending upon the context in which it is used, a combination implantable neurological stimulator and drug pump or drug delivery device.

Augmentation of sacral nerve stimulation with pudendal nerve stimulation and/or targeted drug delivery to a target tissue volume is capable of providing certain advantages and may help the patient achieve better clinical outcomes. For example, the nerve integrity of some patients may be compromised due to the progression of a neurological disease such as multiple sclerosis or Parkinson's disease. Other patients may have compromised nerves due to injury caused by obstetrics or accidents. In the case of a compromised neurological system in the pelvic floor, signal conduction may be a major issue and a factor in their incontinence. Because the pelvic floor is innervated by nerve fibers from each of the sacral nerves, stimulation of a single sacral nerve does not always give adequate or full relief of the patient's incontinence.

Stimulation of and/or drug delivery to both the sacral nerve and the pudendal nerve provides broader electrical stimulation and drug infusion patterns covering more of the pelvic floor and may result in additional relief of the incontinence symptoms. In addition to the sacral nerves, the pudendal and other nerves described herein are good sites to stimulate and/or deliver drugs to because they innervate much of the pelvic floor, including the urinary sphincters.

The sacral nerves innervate the pelvic floor and the legs and feet. Stimulation of the sacral nerve results in stimulation of both the pelvic floor and the leg and foot. One issue that many sacral nerve stimulation patients experience is an annoying stimulation of the leg and/or foot, which at times may be mitigated through reducing the stimulation level on the sacral nerve. An advantage to stimulating both the sacral nerve and the pudendal nerve is that lower stimulation levels may be used to achieve the same or better therapeutic results which may eliminate the annoying stimulation of the leg and/or foot. The lower stimulation levels can result in less sensory stimulation and in the patient being less aware of the presence of the stimulation. An additional advantage is that lower electrical stimulation levels increase the life of the battery powering the implanted pulse generator.

According to one embodiment of the present invention, electrical stimulation of and/or drug delivery to the sacral nerves and/or the pudendal nerves is lateralized. That is, electrical stimulation of and/or drug delivery to the sacral and/or pudendal nerves occurs on opposite sides. For example, the sacral nerve may be electrically stimulated on the left side while a drug is delivered to the pudendal nerve on the right side. The amount and degree of nerve laterilization is preferably determined by looking to factors such as nerve EMG response, anatomical access, physician preference and patient preference.

FIG. 1 shows one embodiment of the present invention, where INS 10 is a combination implantable pulse generator and drug pump implanted in an upper buttock position in a patient, lead 18 is implanted near or adjacent to pudendal nerve or nerve portion 26, and drug delivery catheter 300 is implanted near or adjacent to sacral nerve or nerve portion 25, to thereby effect therapeutic relief. Hermetically sealed enclosure 14 is preferably formed of a biocompatible material such as an appropriate metal alloy containing titanium. In addition to housing circuitry for effecting electrical stimulation of the pelvic floor, INS 10 of FIG. 1 also contains circuitry and mechanisms for holding one or more drugs in a reservoir and delivering such drugs to a target tissue volume via drug catheter 300.

FIG. 1 shows the distal end of lead 18 implanted near or adjacent to pudendal nerve or nerve portion 26, and the distal end of drug catheter 300 implanted near or adjacent to sacral nerve 25 or a sacral nerve portion, to thereby effect therapeutic relief. Note, however, that INS 10 may be implanted in any appropriate location in the patient, such as in the abdomen or side. Note further that the positions of the distal ends of catheter 300 and lead 18 may be exchanged such that a drug is delivered in close proximity to pudendal nerve or nerve portion 26 while sacral nerve 25 is electrically stimulated.

Relief is effected by INS 10 and lead 18 as a result of electrical stimulation signals being delivered to or near sacral nerve 25 or nerve portion 8 by electrodes 40-43, and to or near pudendal nerve 26 or nerve portion 8 by electrodes 40-43, as well as by one or more drugs being delivered to the distal end of catheter 300, the target tissue volume in proximity to the distal end of drug catheter 300 being infused with such drugs through the action of the drug pump component of INS 10/drug pump 314.

One, two, three, four or more electrodes 40, 41, 42 and 43 may be disposed at the distal end of lead 18. FIG. 1 shows four electrodes located at the distal end of lead 18 near pudendal nerve 26. Other lead locations, electrode configurations and lead configurations are possible and contemplated in the present invention.

Drug catheter 300 may possess more than one port at or near the distal end thereof for the infusion of drugs into a tissue volume in proximity to such port. Indeed, such ports may be disposed anywhere along the length of catheter 300 according to the requirements at hand and the disease being treated. Drug catheter 300 may be formed from any of many different, well-known, suitable biocompatible materials, such polyurethane, and may contain one, two, three or more lumens disposed therewithin for carrying drugs to the ports and catheter locations associated therewith.

In one embodiment of the present invention, lead 18 provides electrical stimulation pulses to the desired nerve target site or portion 26 and thereby stimulates the target nerve or nerve portion located in the vicinity of the electrode(s) thereof. Lead 18 may have unipolar electrodes disposed thereon (where enclosure 14 is employed as an indifferent electrode) or may have bipolar electrodes disposed thereon, where one or more electrodes disposed on a lead are employed as the indifferent electrode. In one embodiment of the present invention, Lead 18 extends from lead connector 13, which in turn forms an integral portion of lead extension 15 connected at its proximal end to connector header module 12.

Typically, catheter 300 and lead 18 are tunneled subcutaneously between the location of INS 10 and the location or site of the nerve or nerve portion 26 that is to be stimulated. INS 10 is typically implanted in a subcutaneous pocket formed beneath the patient's skin according to methods well known in the art. Further details concerning various methods of implanting INS 10 and lead and 18 are disclosed in the Medtronic Interstim Therapy Reference Guide published in 1999, the entirety of which is hereby incorporated by reference herein. Other known methods of implanting and locating catheter 300 and lead 18 are of course contemplated in the present invention.

Some representative examples of lead 18 include MEDTRONIC nerve stimulation lead model numbers 3080, 3086, 3092, 3487, 3966 and 4350 as described in the MEDTRONIC Instruction for Use Manuals thereof, all hereby incorporated by reference herein, each in its respective entirety. Some representative examples of INS 10 include MEDTRONIC implantable electrical stimulator model numbers 3023, 7424, 7425 and 7427 as described in the Instructions for Use Manuals thereof, all hereby incorporated by reference herein, each in its respective entirety. INS 10 may also be constructed or operate in accordance with at least some portions of the implantable stimulators disclosed in U.S. Pat. No. 5,199,428 to Obel et al., U.S. Pat. No. 5,207,218 to Carpentier et al., or U.S. Pat. No. 5,330,507 to Schwartz, all of which are hereby incorporated by reference herein, each in its respective entirety.

U.S. patent application Ser. No. 10/004,732 entitled "Implantable Medical Electrical Stimulation Lead Fixation Method and Apparatus" and Ser. No. 09/713,598 entitled "Minimally Invasive Apparatus for Implanting a Sacral Stimulation Lead" to Mamo et al., the respective entireties of which are hereby incorporated by reference herein, describe methods of percutaneously introducing lead 18 to a desired nerve stimulation site in a patient.

Certain aspects of the subject matter described in U.S. Provisional Patent Application Ser. No. 60/459,077 entitled "Method, System and Device for Treating Disorders of the Pelvic Floor by means of Electrical Stimulation of the Pudendal and Associated Nerves, and the Optional Delivery of Drugs in association," the entirety of which is hereby incorporated by reference herein, where various methods of positioning and implanting a medical electrical lead 18 so as to provide optimal stimulation of the pudendal nerve 26 or a portion thereof are described, may be adapted for use in conjunction with at least some embodiments of the present invention.

Figure 2:
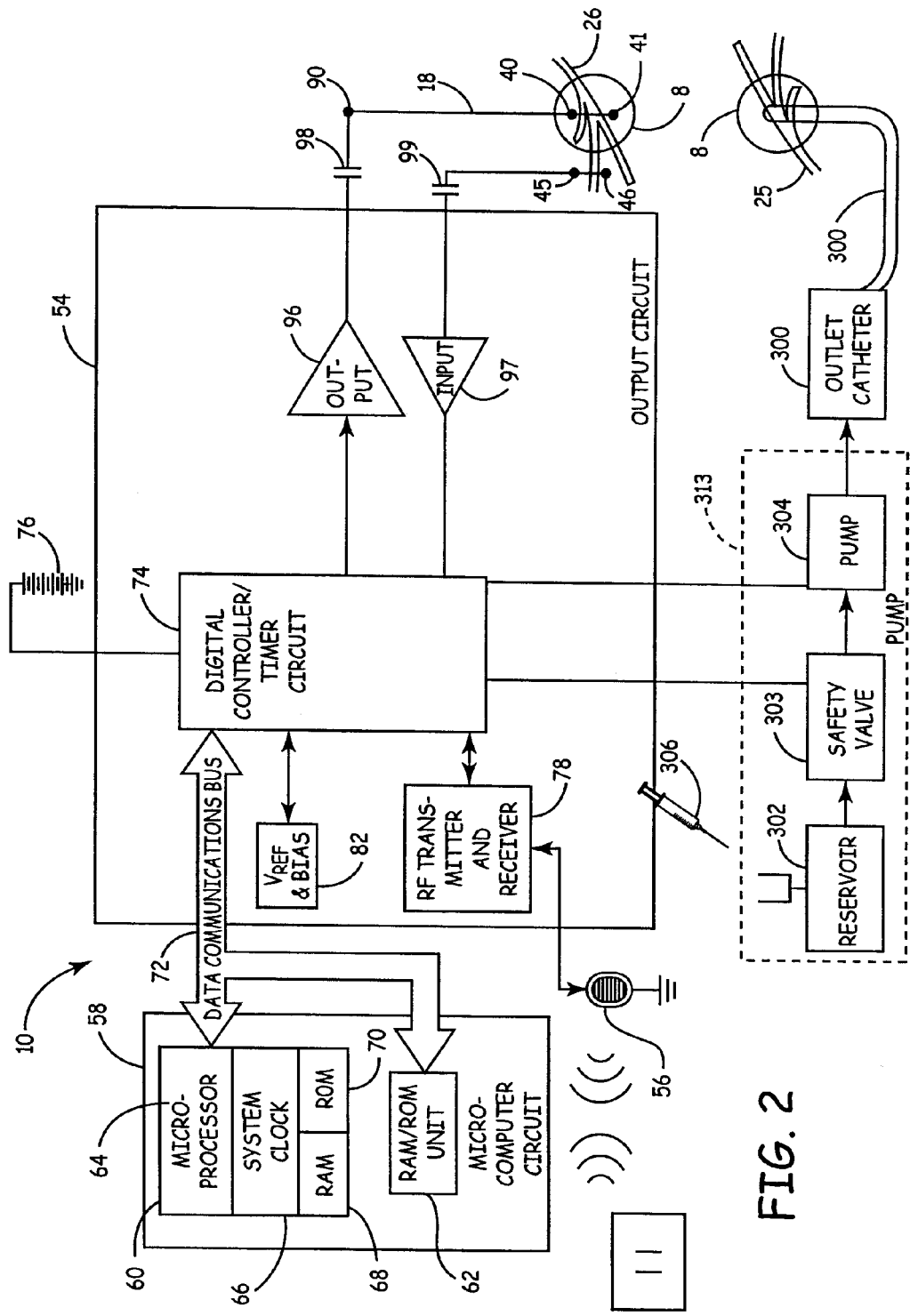
FIG. 2 shows a block diagram illustrating some of the constituent components of INS 10 in accordance with one embodiment of the present invention illustrated in FIG. 1.

FIG. 2 shows a block diagram illustrating some of the constituent components of INS 10 in accordance with one embodiment of the present invention, where INS 10 is a combined implantable electrical stimulator and drug pump having a microprocessor- or controller-based architecture. Other architectures of INS 10 are of course contemplated in the present invention, such as the logic or state machine architecture employed in the Medtronic Model Number 3023 INS. For the sake of convenience, INS 10 in FIG. 2 is shown with one catheter 300 and one 18 connected thereto; similar circuitry and connections not shown in FIG. 2 apply generally to other possible additional leads and catheters not shown in the drawings.

INS 10 may be an open-loop non-feedback-control system, or a closed-loop feedback control system. In the case of a closed-loop feedback control embodiment of the present invention, FIG. 2 shows optional input amplifier 97 connected to sensing electrodes 45 and 46 through capacitor 99. Similarly, feedback sensors may be employed to control the delivery of drugs to the patient from drug pump portion 313.

In the embodiment of the present invention shown in FIG. 2, drug pump portion 313 in FIG. 2 comprises drug reservoir 302, safety valve 303 and pump 304. The proximal end of outlet catheter 300 is connected to drug pump 304. Outlet catheter 300 has a discharge port located at the distal end thereof, which is located in proximity to a tissue volume intended to be treated with the drug disposed in reservoir 302. In accordance with well-known methods and devices known in the art, needle 306 is employed to refill reservoir 302 through an inlet port connected to reservoir 302. Note that drug pump portion 313 may contain multiple reservoirs, safety valves, pumps, and outlet catheters. Digital controller/timer circuit 74 and micro-computer circuit 58 control the operation of drug pump portion 313, most preferably according to particularized instructions programmed within microcomputer circuit 58 by a health care provider. In some embodiments of the present invention, one or more drugs are dispensed through catheter 300 upon receiving a patient-activated command. Micro-computer 58 is preferably programmed by a health care provider to lock out patient-activated commands that occur during periods of time when drugs should not be dispensed.

INS 10 in FIG. 2 is most preferably programmable by means of external programming unit 11. One such programmer is the commercially available Medtronic Model No. 7432 programmer, which is microprocessor-based and provides a series of encoded signals to INS 10, typically through a programming head which transmits or telemeters radio-frequency (RF) encoded signals to INS 10. Another suitable programmer is the commercially available Medtronic Model No. 8840 programmer, which is also microprocessor-based but features a touch control screen. Any of a number of suitable programming and telemetry methodologies known in the art may be employed so long as the desired information is transmitted to and from the implantable electrical stimulator 10.

As shown in FIG. 2, lead 18 is coupled to a node in INS 10 through capacitor 98. Microcomputer circuit 58 preferably comprises on-board circuit 60 and off-board circuit 62. By way of example, circuit 58 may correspond to a microcomputer circuit disclosed in U.S. Pat. No. 5,312,453 to Shelton et al., hereby incorporated by reference herein in its entirety. On-board circuit 60 preferably includes microprocessor 64, system clock circuit 66 and on-board RAM 68 and ROM 70. Off-board circuit 62 preferably comprises a RAM/ROM unit. On-board circuit 60 and off-board circuit 62 are each coupled by data communication bus 72 to digital controller/timer circuit 74. Microcomputer circuit 58 may comprise a custom integrated circuit device augmented by standard RAM/ROM components.

Electrical components shown in FIG. 2 are powered by an appropriate implantable primary (i.e., non-rechargeable) battery power source 76 or secondary (i.e., rechargeable) battery power source 76. For the sake of clarity, the coupling of battery 76 to the various components of INS 10 is not shown in FIG. 2. Antenna 56 is connected to microcomputer circuit 58 via digital controller/timer circuit 74 and data communication bus 72 to permit uplink/downlink telemetry through RF transmitter and receiver telemetry unit 78. By way of example, telemetry unit 78 may correspond to that disclosed in U.S. Pat. No. 4,566,063 issued to Thompson et al. It is generally preferred that the particular programming and telemetry scheme selected permit the entry and storage of electrical stimulation parameters. The specific embodiments of antenna 56 and other telemetry circuitry presented herein are shown for illustrative purposes only, and are not intended to limit the scope of the present invention.

Continuing to refer to FIG. 2, $V_{REF}$ and bias circuit 82 most preferably generate stable voltage reference and bias currents for analog circuits included in output circuit 54. Operating commands for controlling the timing of INS 10 are coupled by data bus 72 to digital controller/timer circuit 74, where digital timers and counters establish the specific stimulation parameters of INS 10 as well as various timing windows for controlling the operation of peripheral components disposed within input/output circuit 54. Output pulse generator 96 provides electrical stimuli to desired nerve and/or nerve portion 25 or 26 through coupling capacitor 98 in response to a trigger signal provided by digital controller/timer circuit 74, when an externally transmitted stimulation command is received, or when a response to other stored commands is received.

By way of example, output amplifier 96 may correspond generally to an output amplifier disclosed in U.S. Pat. No. 4,476,868 to Thompson, hereby incorporated by reference herein in its entirety. The specific embodiments of output amplifier 96 identified herein are presented for illustrative purposes only, and are not intended to be limiting in respect of the scope of the present invention. The specific embodiments of such circuits may not be critical to practicing some embodiments of the present invention so long as they provide means for generating an appropriate train of stimulating pulses to desired nerve or nerve portion 25 and/or 26.

In various embodiments of the present invention, INS 10 may be programmably configured to operate so that it varies the rate at which it delivers stimulating pulses to desired nerve or nerve portion 25 and/or 26, and/or to vary the rate or manner at which outlet catheter 300 delivers one or more drugs to a desired tissue volume, in response to one or more selected outputs being generated, or in response to one or more signals of interest being detected by one or more sensors. INS 10 may further be programmably configured to operate so that it may vary the morphology of the stimulating electrical and/or drug output pulses it delivers. Numerous implantable electrical stimulator features and functions not explicitly mentioned herein may be incorporated into INS 10 while remaining within the scope of the present invention. Various embodiments of the present invention may be practiced in conjunction with one, two, three or more leads, in conjunction with one, two, three, four or more electrodes disposed on each lead, or in conjunction with one, two, three or more outlet catheters connected thereto.

Leadless embodiments of the present invention are also contemplated, where one or more electrical stimulation, drug pump or other type of drug delivery device, and/or sensing electrode capsules or modules are implanted at or near a desired nerve or nerve portion 25 and/or 26, and the capsules or modules deliver electrical stimuli or drugs directly to the selected site using a preprogrammed stimulation or drug delivery regime, and/or the capsules or modules sense electrical, chemical or other pertinent signals for monitoring and feedback control purposes. Such capsules or modules are preferably powered by rechargeable batteries that may be recharged by an external battery charger using well-known inductive coil or antenna recharging means, and preferably contain electronic circuitry sufficient to permit telemetric communication with a programmer, to deliver electrical stimuli and/or sense electrical or other signals, and to store and execute instructions or data received from the programmer. Alternatively, in one embodiment of the present invention INS 10 is configured to recharge such a remotely positioned capsule or module by RF means on a periodic basis according to battery state of charge requirements measured or exhibited by such remote capsule or module.

Examples of methods and devices that may be adapted for use in the wireless devices and methods of the present invention include those described in U.S. Pat. No. 6,208,894 to Schulman et al. entitled "System of implantable devices for monitoring and/or affecting body parameters;" U.S. Pat. No. 5,876,425 to Schulman et al. entitled "Power control loop for implantable tissue stimulator;" U.S. Pat. No. 5,957,958 to Schulman et al. entitled "Implantable electrode arrays;" U.S. patent application Ser. No. 09/030,106 filed Feb. 25, 1998 to Schulman et al. entitled "Battery-Powered Patient Implantable Device;" and U.S. Pat. No. 6,650,943 to Whitehurst et al. entitled "Fully Implantable Neurostimulator for Cavernous Nerve Stimulation as a Therapy for Erectile Dysfunction and Other Sexual Dysfunction."

Figure 3:
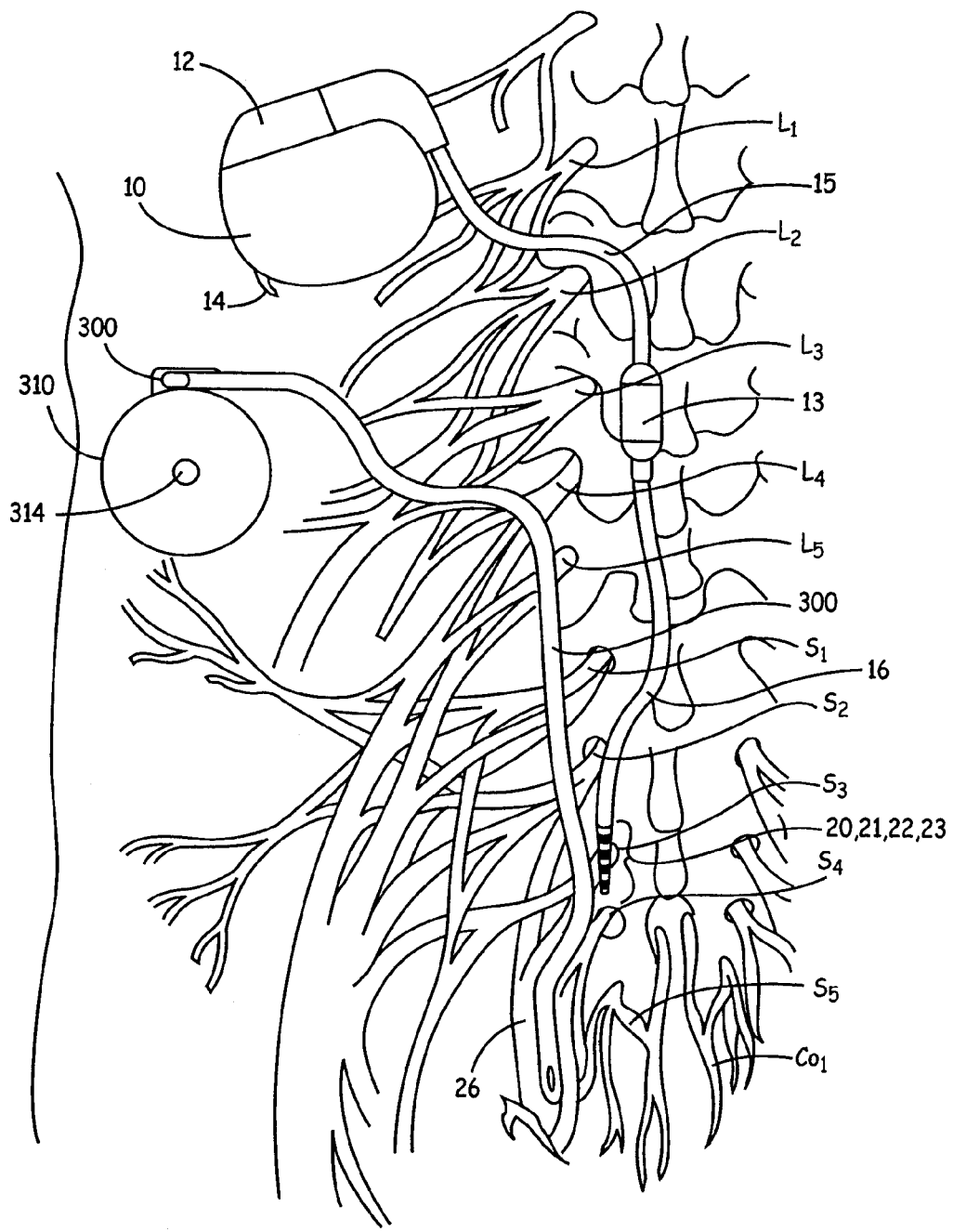
FIG. 3 shows a simplified anatomical view of portions of the pelvic floor of a human patient, the locations of sacral and associated nerves therein, and illustrative positionings of INS 10, drug pump or delivery device 310, electrical stimulation lead 16 and corresponding electrodes 20-23, and drug delivery catheter 300.

FIG. 3 shows a simplified anatomical view of portions of the pelvic floor of a human patient, the locations of sacral and associated nerves therein, and illustrative positionings of INS 10, drug pump or delivery device 310, electrical stimulation lead 16, corresponding electrodes 20-23, and drug delivery catheter 300. FIG. 3 shows INS 10 implanted in an appropriate location within the patient, with lead 16 being implanted near or adjacent to one or more of sacral nerves S1, S2, S3, and/or S4, and the distal end of outlet catheter implanted near or adjacent to sacral nerve or nerve portion 25 to thereby effect therapeutic relief. Such relief is effected as a result of electrical stimulation signals and drugs being delivered to or near to or near one or more of such nerves S1, S2, S3 25, S4, and/or pudendal nerve or nerve portion 26, or a nerve(s) in proximity thereto, by electrodes 20, 21, 22, and/or 23 and outlet catheter 300. One, two, three, four or more electrodes 20, 21, 22 and 23 may be disposed at the distal end of lead 16. A second electrical stimulation lead 18, not shown in FIG. 2, having one, two, three, four or more electrodes 40, 41, 42 and 43 may be employed to electrically stimulate nerve or nerve portion 25 or 26, according to the particular requirements at hand. Consistent with the foregoing description, other lead locations, electrode configurations and outlet catheter configurations are of course possible and contemplated in the present invention. For example, leads 16, 18 may be implanted adjacent left and a right sacral nerve or nerve portions, respective, adjacent left and a right pudendal nerve or nerve portions, respectively, or adjacent a sacral nerve or nerve portion and a pudendal nerve or nerve portion, respectively.

Figure 4:
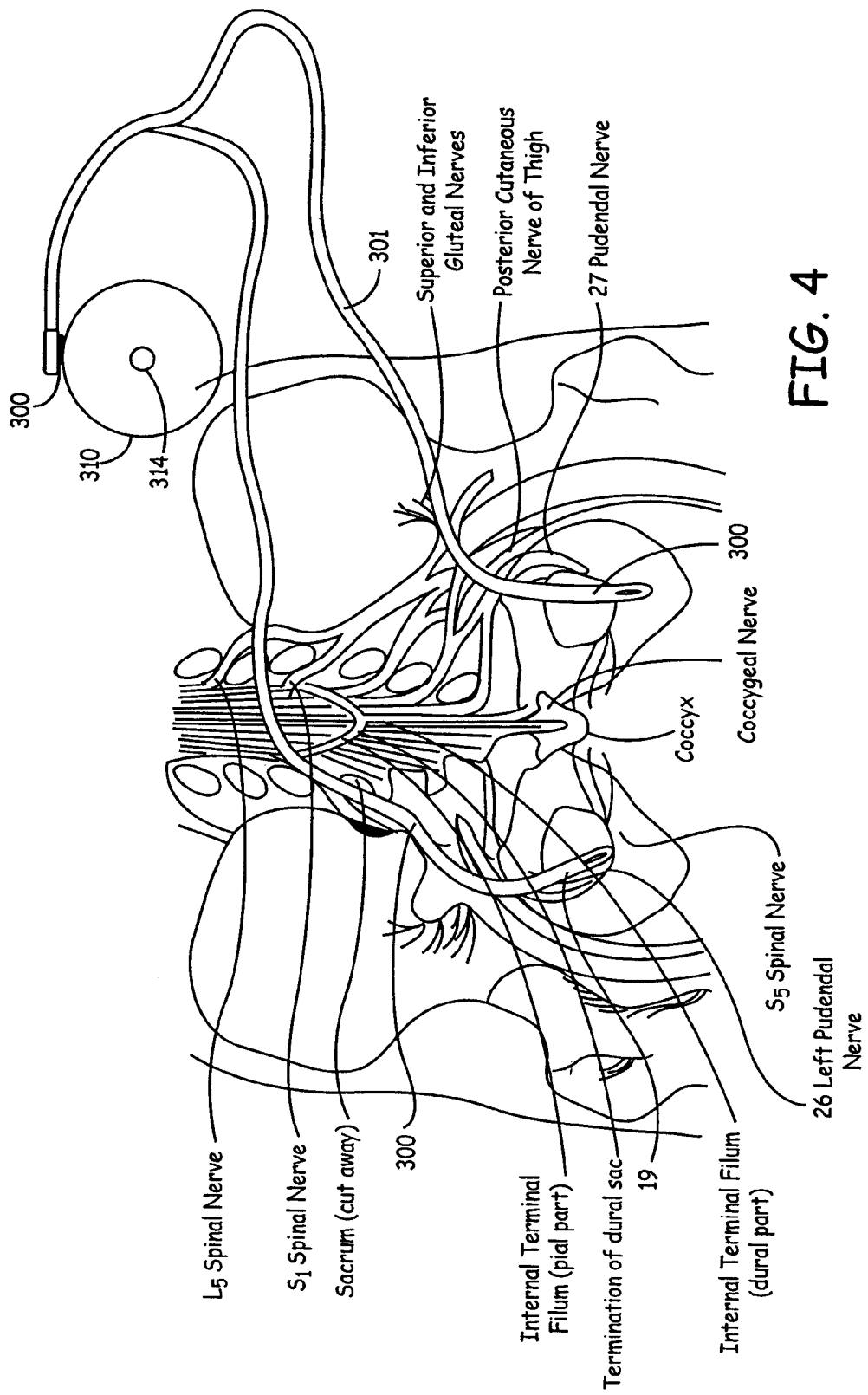
FIG. 4 shows a simplified anatomical view of the pelvic floor of a female human patient, the locations of the left and right pudendal nerves 26 and 27 and associated nerves therein, the positioning of drug pump or delivery device 310, and the positioning of drug delivery catheters 300 and 301 such that the distal portions thereof are located near left and right pudendal nerves 26 and 27.

FIG. 4 shows a simplified anatomical view of the pelvic floor of a female human patient, the locations of the left and right pudendal nerves 26 and 27 and associated nerves therein, the positioning of drug pump or delivery device 310, and the positioning of drug delivery catheters 300 and 301 such that the distal portions thereof are located near left and right pudendal nerves 26 and 27. Note that the distal ends of drug delivery or outlet catheters 300 and 301 may also be located near sacral nerve(s) or nerve portion(s) 25, and that various permutations and combinations of locations near or at pudendal nerves or nerve portions 26 and sacral nerve or nerve portions 25 are also contemplated in the present invention.

As shown in FIG. 4, pudendal nerve or nerve portion 26 innervates the pelvic floor muscle and sphincters. FIG. 4 shows INS 10 implanted in an appropriate location within the patient, with drug delivery catheters 300 and 301 being implanted near or adjacent to one or more of left pudendal nerve or nerve portion 26 and right pudendal nerve or nerve portion 27, to thereby effect therapeutic relief. Such relief is effected as a result of an appropriate amount of drug being delivered to the desired tissue volume(s) according to an appropriate schedule time regime, where such tissue volumes are in proximity to the desired nerve or nerve portion. Consistent with the foregoing description, other drug delivery catheter locations and configurations are of course possible and contemplated in the present invention.

Figure 5:
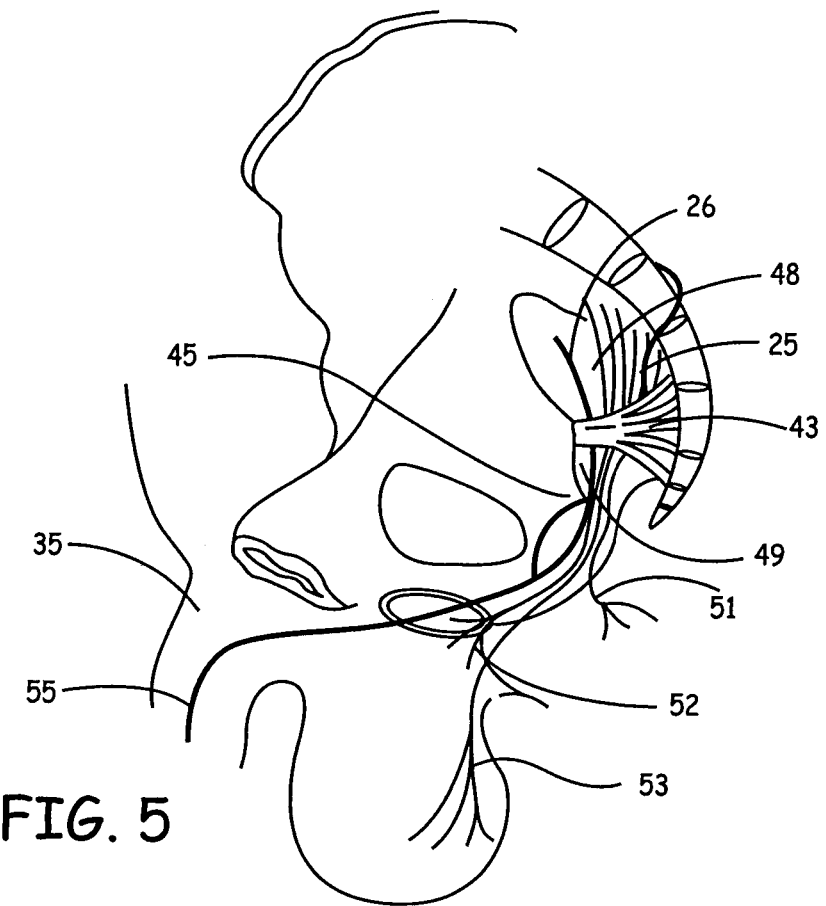
FIG. 5 shows a simplified male anatomical view of the pelvic floor and the locations of the pudendal, sacral and associated nerves therein.

FIG. 5 shows a simplified male anatomical view of the pelvic floor and the locations of pudendal nerve 26 and nerves associated therewith, where in accordance with some embodiments of the present invention leads 16 and/or 18, electrodes 20-23 and/or 40-43, and drug delivery catheters 300 and 301 may be attached, connected or implanted in proximity thereto. Pudendal nerve 26 may be seen to extend downwardly past sacrospinal ligament 43, greater sciatic foramen 48, and lesser sciatic foramen 49, and thereafter to branch into inferior rectal nerves 51, perineal nerves 52, scrotal nerves 53 and dorsal nerve 55 of penis 35.

Figure 6:
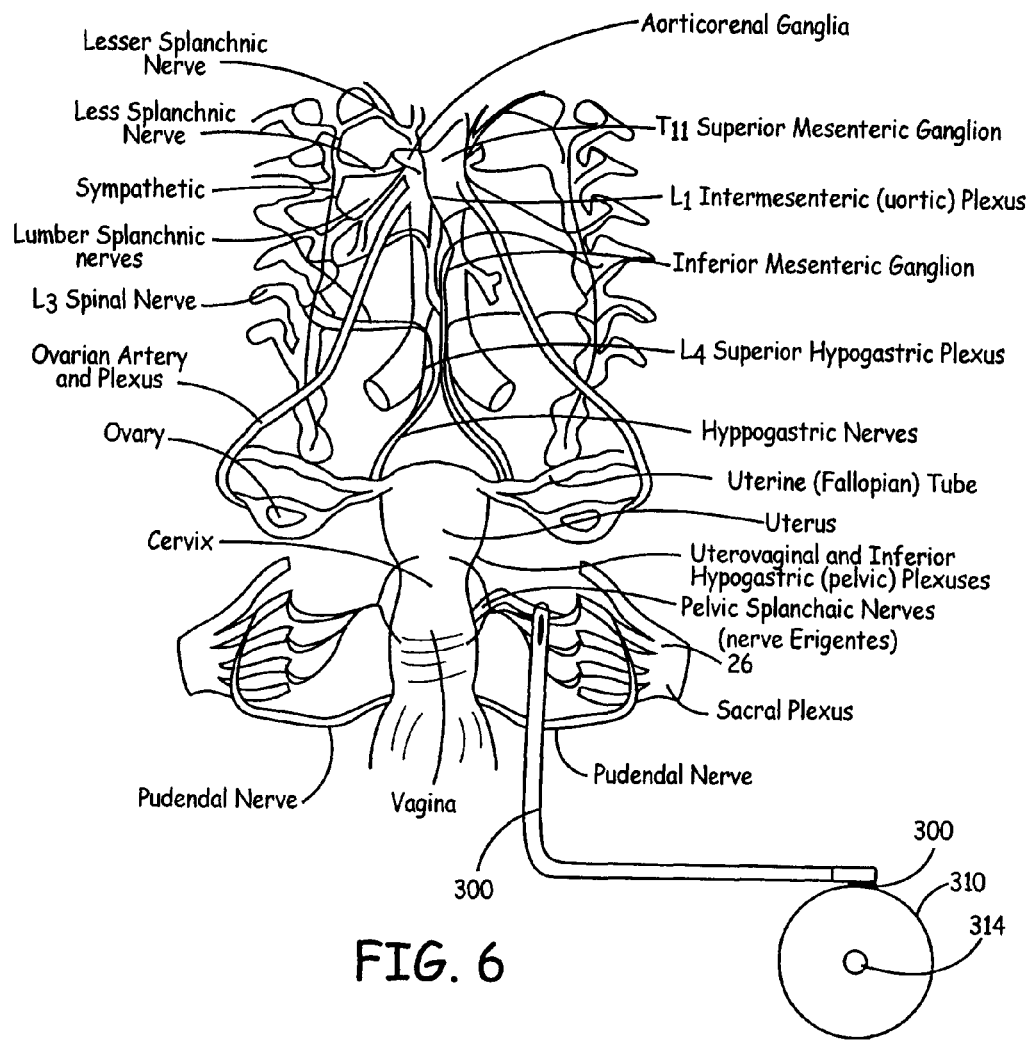
FIG. 6 shows a simplified anatomical view of the pelvic floor of a female human patient, the locations of the sacral nerves 25 and associated nerves therein, the positioning of drug pump or delivery device 310, and the positioning of drug delivery catheter 300 such that the distal portion thereof is located near one or more sacral nerves or nerve portions 25.

FIG. 6 shows a simplified anatomical view of the pelvic floor of a female human patient, the locations of the sacral nerves and nerve portions 25 and associated nerves therein, the positioning of drug pump or delivery device 310, and the positioning of drug delivery catheter 300 such that the distal portion thereof is located near one or more sacral nerves or nerve portions 25. Other sites or tissue volumes to which one or more drugs may be delivered by drug pump 300 and drug delivery catheter 301 are also illustrated in FIG. 6, such as the lesser splanchnic nerve or nerve portion, the least splanchnic nerve or nerve portion, the sympathetic trunk nerve or nerve portion, the lumbar splanchnic nerve or nerve portion, the L1, L2, L3, L4, etc, spinal nerve or nerve portion, the ovarian plexus, aorticorneal ganglia, the superior mesenteric ganglion, the intermesenteric (aortic) plexus, the superior hypogastric nerves or nerve portions, the uterovaginal plexus, the inferior hypogastric plexus, one or more of the pelvic splanchnic nerves or nerve portions.

Figure 7:
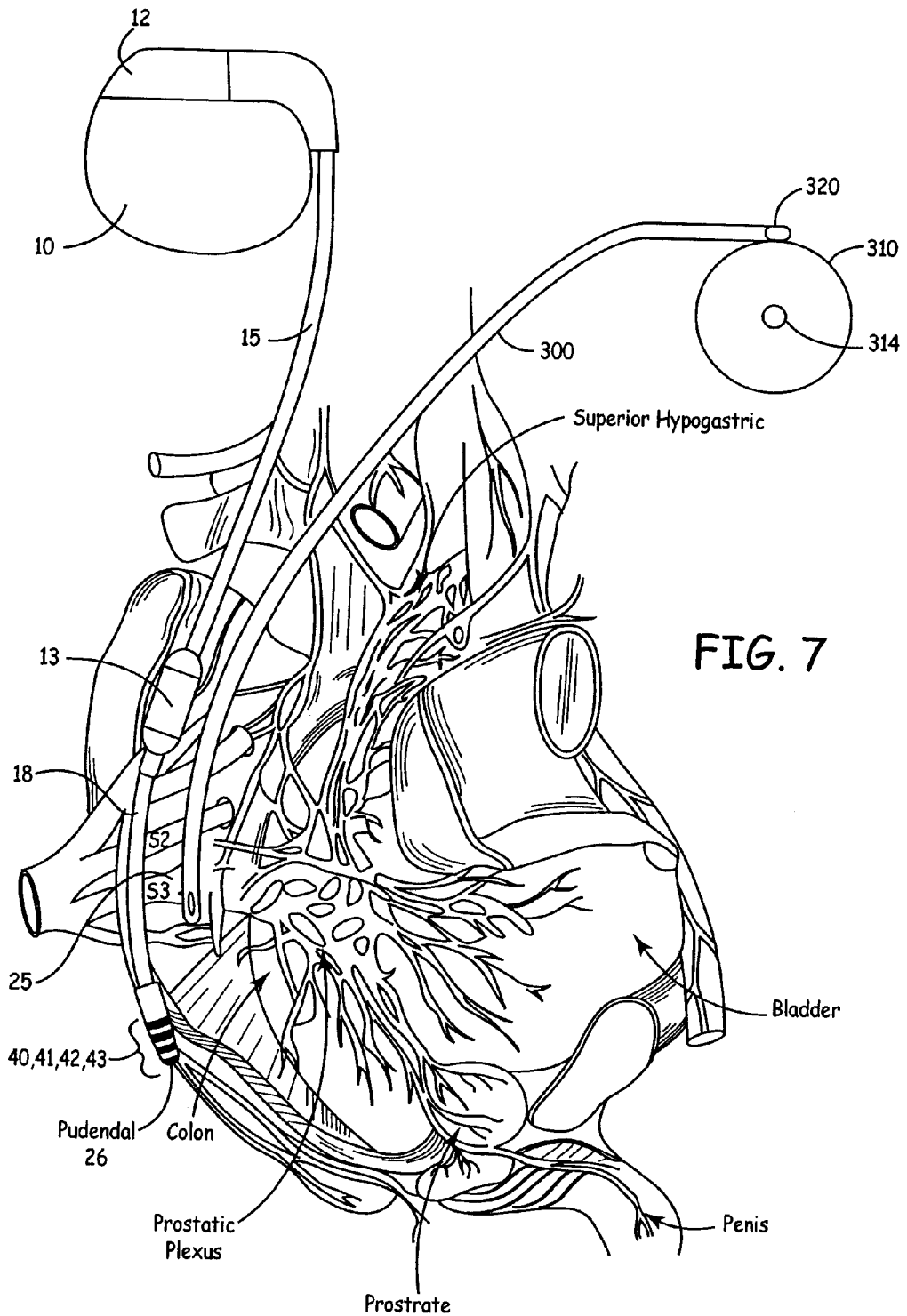
FIG. 7 shows a simplified anatomical view of portions of the pelvic floor of a male human patient, the locations of pudendal and associated nerves 26, the locations of sacral and associated nerves 25, and illustrative positionings of INS 10, electrical stimulation lead 16 and corresponding electrodes 20-23, drug pump or delivery device 310, and drug delivery catheter 300.

FIG. 7 shows a simplified anatomical view of portions of the pelvic floor of a male human patient, the locations of pudendal and associated nerves 26, the locations of sacral and associated nerves 25, and illustrative positionings of INS 10, electrical stimulation lead 18 and corresponding electrodes 40-43, drug pump or delivery device 310, and drug delivery catheter 300. In FIG. 7, the distal end of drug delivery catheter 300 is located near or at the prostatic plexus. Other sites or tissue volumes to which one or more drugs may be delivered by drug pump 300 and drug delivery catheter 301 are also illustrated in FIG. 7, such as the prostate, the bladder, the penis, and the superior hypogastric nerves or nerve portions. Many locations within a patient's body may be electrically stimulated or infused with one or more drugs in accordance with various embodiments of the present invention, including, but not limited to, a sacral nerve or branches or portions thereof, a pudendal nerve or branches or portions thereof, a hypogastric nerve or branches or portions thereof, a prostatic plexus nerve or branches or portions thereof, a sacral splanchnic nerve or branches or portions thereof, a pelvic splanchnic nerve or branches or portions thereof, the prostate or branches or portions thereof, the pelvic floor, the colon or branches or portions thereof, the bladder or portions thereof, the vagina or portions thereof, the anus or portions thereof, the external anal sphincter or portions thereof, the urethra or portions thereof, the penile dorsal nerve or portions thereof, inferior rectal nerves or branches or portions thereof, perineal nerves or branches or portions thereof, scrotal nerves or branches or portions thereof, the scrotum or portions thereof, Alcock's Canal or branches or portions thereof, sacro-tuberous ligament or branches or portions thereof, ischial tuberosity or branches or portions thereof, greater sciatic foramen or branches or portions thereof, or lesser sciatic foramen or branches or portions thereof.

Figure 8A:
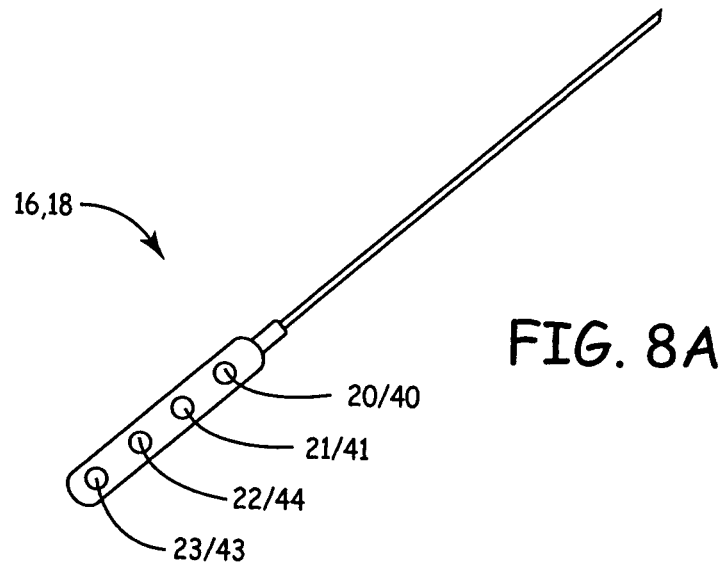
FIGS. 8A through 8E show various embodiments of the distal end of leads 16 and 18 of the present invention.
Figure 8B:
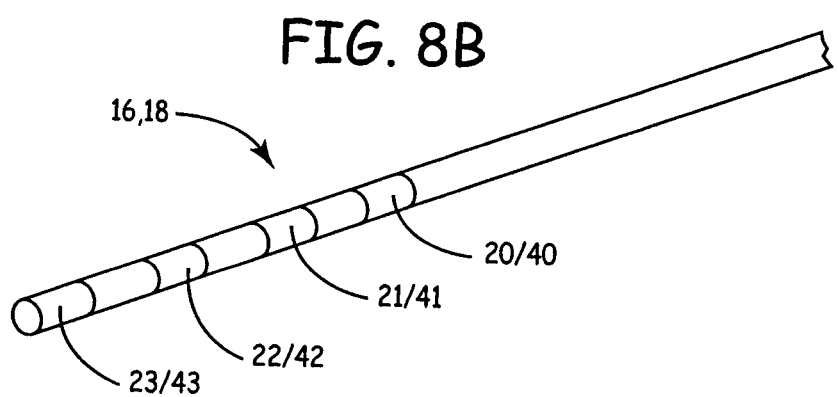

FIGS. 8A through 8E show various embodiments of a distal end of medical electrical lead 16 and/or 18 of the present invention. In FIG. 8A, lead 16/18 is a paddle lead having electrodes 20-23 arranged along an outwardly facing planar surface. Such a paddle lead 16/18 is preferably employed to stimulate peripheral nerves. In FIG. 8B, lead 16/18 is a conventional quadrapolar lead having no pre-attached anchoring mechanism 19. Electrodes 20-23 are cylindrical in shape and extend around the circumference of the lead body.

Figure 8C:
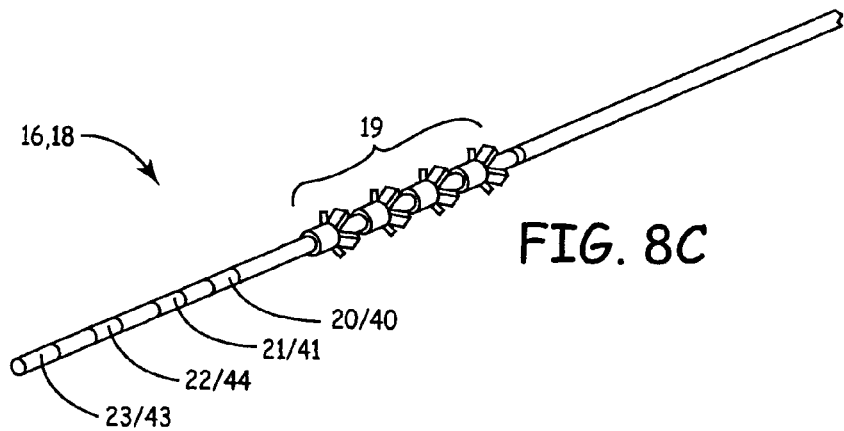

In FIG. 8C, lead 16/18 is a quadrapolar lead having tined lead anchors 19. Tines 19 may be formed from flexible or rigid biocompatible materials in accordance with the desired application. Representative examples of some tined and other types of leads suitable, adaptable or modifiable for use in conjunction with the systems, methods and devices of the present invention include those disclosed in U.S. patent application Ser. No. 10/004,732 entitled "Implantable Medical Electrical Stimulation Lead Fixation Method and Apparatus" and Ser. No. 09/713,598 entitled "Minimally Invasive Apparatus for Implanting a Sacral Stimulation Lead" to Mamo et al., as well as those disclosed in U.S. Pat. No. 3,902,501 to Citron entitled "Endocardial Lead," U.S. Pat. No. 4,106,512 to Bisping entitled "Transvenously Implantable Lead," and U.S. Pat. No. 5,300,107 to Stokes entitled "Universal Tined Myocardial Pacing Lead."

Figure 8D:
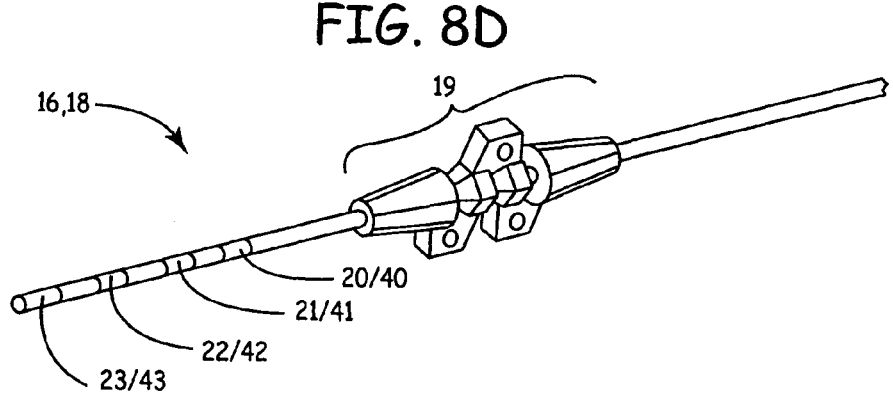
Figure 8E:
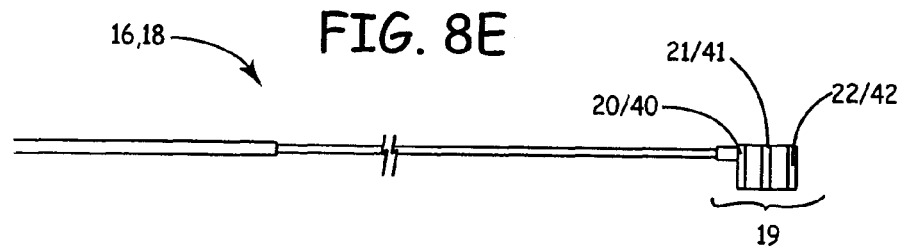

In FIG. 8D, lead 16/18 is a quadrapolar lead having pre-attached suture anchor 19. In FIG. 8E, lead 16/18 is a tri-polar cuff electrode, where cuff/anchor 19 is wrapped around desired nerve or nerve portion 8 to thereby secure the distal end of lead 16/18 to the nerve and position electrodes 20-22 against or near nerve or nerve portion 25 or 26. The Medtronic Model No. 3995 cuff electrode lead is one example of a lead that may be adapted for use in the present invention, the Instructions for Use manual of which is hereby incorporated by reference herein in its entirety.

Leads 16 and 18 are preferably less than about 5 mm in diameter, and most preferably less than about 1.5 mm in diameter. Polyurethane is a preferred material for forming the lead body of leads 16 and 18, although other materials such as silicone may be employed. Electrical conductors extending between the proximal and distal ends of leads 16 and 18 for supplying electrical current to the electrodes are preferably formed of coiled, braided or stranded wires comprising an MP35N platinum-iridium alloy. Electrodes 20, 21, 22 and 23 and 40, 41, 42 and 43 may be ring electrodes, coiled electrodes, electrodes formed from portions of wire, barbs, hooks, spherically-shaped members, helically-shaped members, or may assume any of a number of different structural configurations well known in the art.

Inter-electrode distances on leads 16 and 18 are preferably about 3 mm, but other inter-electrode distances may be employed such as about 1 mm, about 2 mm, about 4 mm, about 5 mm, about 6 mm, about 7 mm, about 8 mm, about 9 mm, about 10 mm, about 12 mm, about 14 mm, about 16 mm, about 18 mm, about 20 mm, about 25 mm, about 30 mm.

Preferred surface areas of electrodes 20, 21, 22 and 23 and 40, 41, 42 and 43 range between about 1.0 sq. mm and about 100 sq. mm, between about 2.0 sq. mm and about 50 sq. mm, and about 4.0 sq. mm and about 25 sq. mm.

Preferred lengths of electrodes 20, 21, 22 and 23 and 40, 41, 42 and 43 range between about 0.25 mm and about 10 mm, between about 0.50 mm and about 8 mm, and about 1 mm and about 6 mm.

Electrodes 20, 21, 22 and 23 and 40, 41, 42 and 43 are preferably formed of platinum, although other metals and metal alloys may be employed such as stainless steel or gold.

The distal portion of lead 16 extends to a target site or position near a desired nerve or nerve portion 25 and/or 26, and is preferably held in such position by lead anchor 19. Note that lead anchor 19 may assume any of a number of different structural configurations such one or more suture sleeves, cuffs, tines, barbs, hooks, helical screws, tissue in-growth mechanisms, adhesive, polycyanoacrylate, or glue.

One, two, three, four or more electrodes 20, 21, 22 and 23 or 40, 41, 42 and 43 may be disposed at the distal end of lead 16 and/or lead 18. Electrodes 20, 21, 22 and 23 and 40, 41, 42 and 43 are preferably arranged in an axial array, although other types of arrays may be employed such as inter-lead arrays of electrodes between the distal ends of leads 16 and 18 such that nerves or nerve portions 8 disposed between leads 16 and 18 may be stimulated.

Leads 16 and 18 preferably range between about 4 inches and about 20 inches in length, and more particularly may be about 6 inches, about 8 inches, about 10 inches, about 12 inches, about 14 inches, about 16 inches or about 18 inches in length, depending on the location of the site to be stimulated and the distance of INS 10 from such site. Other lead lengths such as less than about 4 inches and more than about 20 inches are also contemplated in the present invention.

Figure 9:
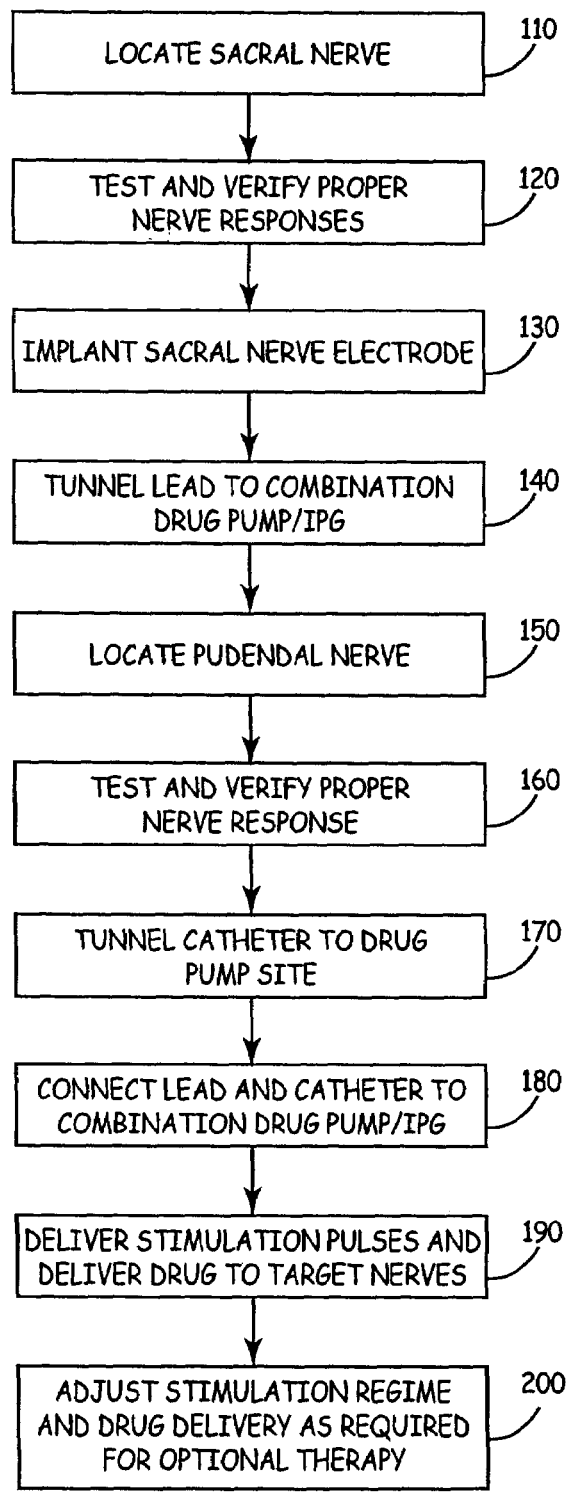
FIG. 9 shows a flow diagram according to one embodiment of a method of the present invention for electrically stimulating at least one of the pudendal and sacral nerves, in combination with delivering one or more drugs to at least one of a sacral nerve 25 and a pudendal nerve 26, associated nerves or portions thereof.

FIG. 9 shows a flow diagram according to one embodiment of a method of the present invention for electrically stimulating one or more sacral nerves or nerve portions 25, and infusing one or more drugs to one or more pudendal nerves or nerve portions 26. Note that the order in which the steps shown in FIG. 9 are carried out may be changed, and that the resulting method will nevertheless fall within the scope of the present invention. In FIG. 9, at step 110 one or more desired sacral nerve electrical stimulation locations are located. Various techniques such as visualization under fluoroscopy or the use of anatomical landmarks may be used to locate the sacral nerve or nerve portion 25 to be stimulated. Step 120 is employed to test and verify proper sacral nerve or nerve portion 25 response prior to implantation of the stimulation electrode. An electrical signal delivered to the nerve through a needle is typically employed to elicit such a nerve response. The nerve response may be detected through a motor response that may be visually detected, a sensory response as reported by the patient or through an electrical response. Following verification of proper nerve response, at step 130 the sacral nerve electrode is implanted. In step 140, INS 10 having drug pump portion 314 disposed therewithin is implanted in an appropriate location within the patient such that the proximal end of lead 16 or 18 may be operably connected thereto, and such that INS 10 is placed in such a location that discomfort and the risk of infection to the patient are minimized.

Step 150 in FIG. 7 is employed to locate the pudendal nerve. Location of pudendal nerve or nerve portion 26 is typically done through the identification of anatomical landmarks. Palpation of the patient as well as usage of fluoroscopy, x-ray and EMG may be employed to assist in proper location of the pudendal nerve. Before or after step 170, INS 10 is implanted in an appropriate location within the patient such that drug delivery catheter 300 may be operably connected thereto, and such that INS 10 is placed in such a location that discomfort and the risk of infection to the patient are minimized. Step 180 is used to operably connect INS 10 to one or more drug delivery catheters 300, which may or may not require the use of an optional lead or catheter extension and catheter connector. In Step 190, INS 10 is activated and stimulation pulses are delivered to electrodes 20, 21, ... n or 40, 41, ... n through lead 16 or 18 to the desired nerve stimulation location 25 or 26 and one or more drugs are delivered via one or more drug delivery catheters 300 to the desired tissue volume(s). In step 200, electrical pulse stimulation and drug delivery parameters are adjusted to optimize the therapy delivered to the patient. Such adjustment may entail one or more of adjusting the number or configuration of electrodes, leads and/or drug delivery catheters used to stimulate or infuse with drugs the selected location, pulse amplitude, pulse frequency, pulse width, pulse morphology (e.g., square wave, triangle wave, sinusoid, biphasic pulse, tri-phasic pulse, etc.), times of day or night when pulses or drugs are delivered, pulse cycling times, the positioning of the lead or leads and/or catheter or catheters, and/or the enablement or disablement of "soft start" or ramp functions respecting the stimulation regime or drug supply regime to be provided. Note that methods of the present invention further contemplate the placement and implantation of multiple electrical stimulation leads and multiple drug delivery catheters.

Figure 10C:
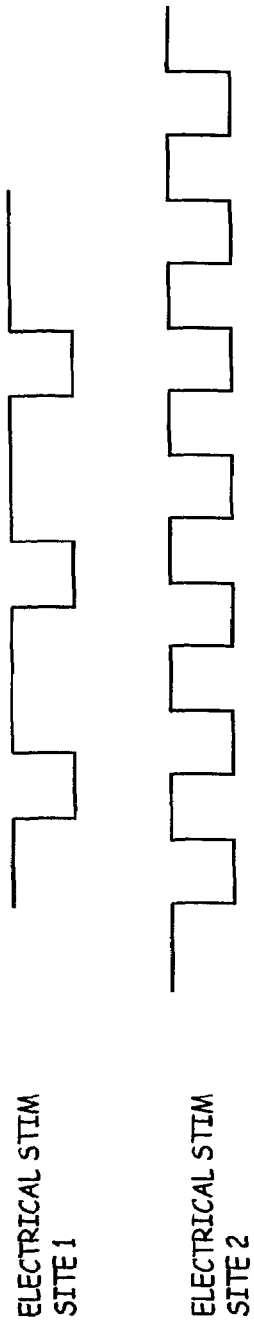
Figure 10D:
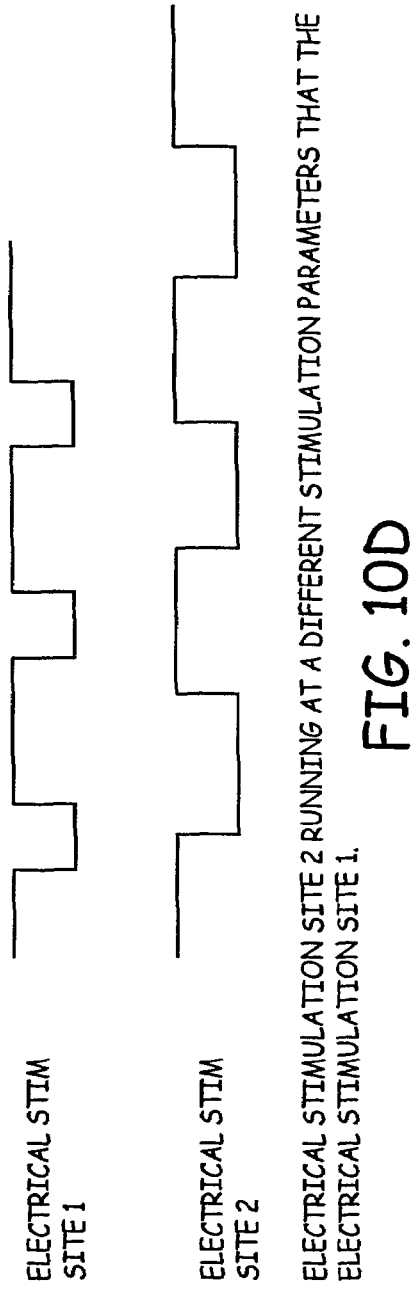
Figure 10E:
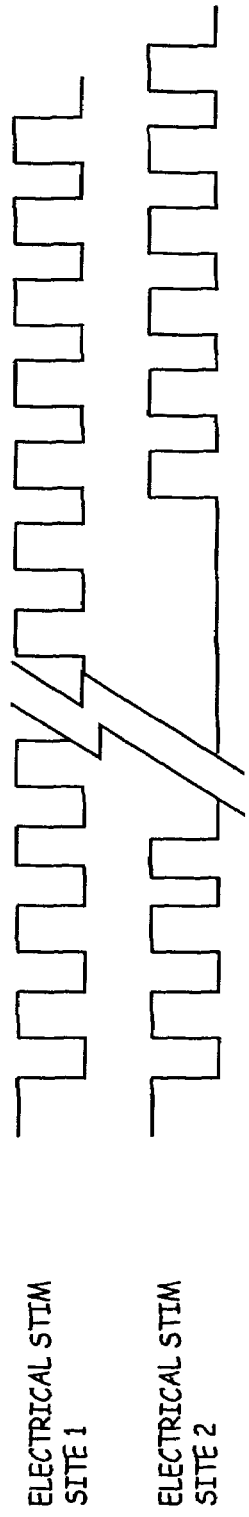
Figure 10F:
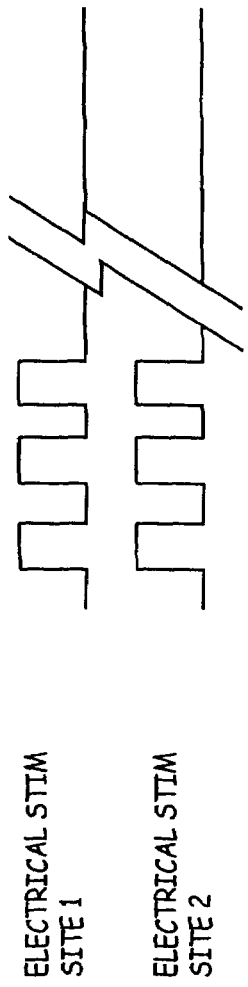

FIGS. 10A through 10F shows various embodiments of the first and second electrical stimulation pulse regimes of the present invention. In FIG. 10A, electrical pulses delivered to a first nerve or nerve portion are synchronized with the electrical pulses delivered to a second nerve or nerve portion. In FIG. 10B, electrical pulses delivered to a first nerve or nerve portion are out of phase in respect of the electrical pulses delivered to a second nerve or nerve portion. In FIG. 10B, the electrical pulses delivered to the first nerve or nerve portion have a lower frequency than the electrical pulses delivered to the second nerve or nerve portion. In FIG. 10D, electrical pulses delivered to a first nerve or nerve portion are characterized in having different stimulation parameters than those of the electrical pulses delivered to a second nerve or nerve portion. In FIG. 10E, electrical pulses are delivered without interruption and on a continuous basis to a first nerve or nerve portion, while the delivery of electrical pulses to a second nerve or nerve portion is suspended for a period of time. In FIG. 10F, electrical pulses are delivered to a first nerve or nerve portion and a second nerve or nerve portion, but at a certain point in time are suspended for a predetermined period of time or until a sensed quantity changes in a predetermined fashion.

Some examples of dual electrical stimulation techniques falling within the scope of the present invention are as follows:

One pulse regime may be delivered continuously, while the other pulse regime is turned on and off in accordance with the patient's symptoms, as such symptoms may wax and wane;

Both pulse regimes may be delivered continuously, one intermittently and the other continuously, or both intermittently;

The two pulse regimes may be different in respect of amplitude, pulse-width, frequency, pulse morphology, and the like;

One or both pulse regimes may be delivered according to a scheduled or detected activity, or according to a predetermined or detected schedule, the activity or schedule having one or more pulse regimes associated therewith, the activities or schedules comprising one or more of circadian rhythms, daytime or nighttime activities or schedules, meals, periods of exercise, periods of sleep, sexual activity, and the like;

One pulse regime may be delivered in accordance with a preprogrammed regime, while the other pulse regime may be delivered, activated, modified and/or terminated via patient activation, modification or termination;

One or both pulse regimes may be delivered between different leads having one or more electrodes each to obtain a spatially broad stimulation pattern;

One or both pulse regimes may be controlled, activated and/or terminated by the patient to customize the delivered therapy.

Some representative ranges of preferred electrical pulse stimulation parameters capable of being delivered by INS 10 through leads 16 and/or 18 include the following:

Frequency: Between about 50 Hz and about 100 Hz;
Between about 10 Hz and about 250 Hz; and
Between about 0.5 Hz and about 500 Hz.
Amplitude: Between about 1 Volt and about 10 Volts;
Between about 0.5 Volts and about 20 Volts; and
Between about 0.1 Volts and about 50 Volts.
Pulse Width Between about 180 microseconds and about 450 microseconds;
Between about 100 microseconds and about 1000 microseconds; and
Between about 10 microseconds and about 5000 microseconds.

In the event multiple signals are employed to stimulate a desired site, the spatial and temporal phase between the signals may be adjusted or varied to produce the desired stimulation pattern or sequence. That is, in the present invention beam forming and specific site targeting via electrode array adjustments are specifically contemplated. Electrode configurations, arrays and stimulation patterns and methods similar to those disclosed by Holsheimer in U.S. Pat. No. 6,421,566 entitled "Selective Dorsal Column Stimulation in SCS, Using Conditioning Pulses," U.S. Pat. No. 5,643,330 entitled "Multichannel Apparatus for Epidural Spinal Cord Stimulation," and U.S. Pat. No. 5,501,703 entitled "Multichannel Apparatus for Epidural Spinal Cord Stimulator," the respective entireties of which are hereby incorporated by reference herein, may also be adapted or modified for use in the present invention. Electrode configurations, arrays, leads, stimulation patterns and methods similar to those disclosed by Thompson in U.S. Pat. No. 5,800,465 entitled "System and Method for Multi-site Steering of Cardiac Stimuli," the entirety of which is hereby incorporated by reference herein, may also be adapted or modified for use in the present invention to permit the steering of electrical fields. Thus, although FIG. 1 shows four electrodes located at the distal end of lead 16 near sacral nerve S3, other lead locations and electrode configurations are possible and contemplated in the present invention.

In various embodiments of the present invention it is contemplated that drugs be delivered to specific sites within a patient using fully implantable or external drug pump devices in combination with providing electrical stimulation to the nerves or nerve portions described above. According to such devices and methods, and as discussed above, drug pump portion 314 may be incorporated into the same housing as INS 10 or, if fully implantable, be separate therefrom in its own hermetically sealed housing. Drug delivery catheter 300 may be attached to drug pump portion 314 of INS 10, or may be attached to a separate implantable or external drug pump through which one or more drugs are delivered to a specific desired target tissue volume. Drug delivery catheter 300 may also be incorporated into lead 16 or 18, or may be separate therefrom. Drugs or therapeutic agents delivered in accordance with this method include, by way of example, antibiotics, pain relief agents such as demerol and morphine, radioactive or radio-therapeutic substances or agents for killing or neutralizing maycer cells, genetic growth factors for encouraging the growth of healthy tissues, drugs for facilitating or encouraging penile or clitoral engorgement, and so forth, more about which we say below.

Drug pumps employed to treat various disease states in accordance with some embodiments of the present invention may be of the well known peristaltic type having reservoirs filled with a liquid containing the drug(s) to be dispensed, or may constitute any of a number of different types of implantable or external drug pump or dispenser types, such as an implantable drug dispenser adapted to deliver drug pellets in solid or semi-solid form to an internal portion of a patient's body at pre-defined intervals. Drug pumps of the present invention may be powered by primary or rechargeable batteries, and may be communicated with or programmed in accordance with telemetry protocols such as those employed in pacemakers or currently marketed implantable drug pumps.

Moreover, in the present invention it is contemplated that drugs be delivered to one or more target tissue volumes in the vicinity of target nerves or branches or portions thereof, as well as into other tissues or voids such as the bladder, one or more smooth muscles, the spinal column, the kidneys, the prostate gland, the testes or testicles, the uterus, the vagina, the penis, the colon, one or more of the pelvic floor muscles, the vascular system, the intestines, the digestive tract, the stomach, the esophagus, or any of a number of different sphincters (e.g., urethral, anal, etc.) or other muscles or organs.

The following issued U.S. patents, all of which are incorporated by reference herein, each in its respective entirety, describe various aspects pertaining to different embodiments of the drug pumps and communication systems of the present invention.

U.S. Pat. No. 4,692,147 to Duggan for "Drug administration device."
U.S. Pat. No. 4,987,897 to Funke for "Body bus medical device communication system."
U.S. Pat. No. 5,083,908 to Gagnebin et al. for "Miniature peristaltic pump."
U.S. Pat. No. 5,382,236 to Otto et al. for "Implantable infusion pump."
U.S. Pat. No. 5,480,656 to Okada et al. for "Prolonged release microcapsules."
U.S. Pat. No. 5,551,849 to Christensen for "Medication delivery device and method of construction."
U.S. Pat. No. 5,609,575 to Larson et al. for "Infusion pump and method with dose-rate calculation."
U.S. Pat. No. 5,639,275 to Baetge for "Delivery of biologically active molecules using cells contained in biocompatible immunoisolatory capsules."
U.S. Pat. No. 5,683,432 to Goedeke for "Adaptive, performance-optimizing communication system for communicating with an implanted medical device."
U.S. Pat. No. 5,733,313 to Barreras et al. for "RF coupled, implantable medical device with rechargeable back-up power source."
U.S. Pat. No. 6,210,368 to Rogers for "Reservoir volume sensors."
U.S. Pat. No. 6,263,246 to Goedeke for "Method and apparatus for communications with an implantable device."
U.S. Pat. No. 6,283,949 to Roorda for "Refillable implantable drug delivery pump."
U.S. Pat. No. 6,322,330 to Thomas for "Compact peristaltic metering pump."
U.S. Pat. No. 6,358,202 to Arent for "Network for implanted computer devices."
U.S. Pat. No. 6,458,118 to Lent et al. for "Drug delivery through microencapsulation."
U.S. Pat. No. 6,471,645 to Warkentin for "Communications system for an implantable device and a drug dispenser."
U.S. Pat. No. 6,485,464 to Christenson et al. for "Reduced height implantable drug infusion device."
U.S. Pat. No. 6,551,290 to Elsberry et al. for "Catheter for target specific drug delivery."
U.S. Pat. No. 6,669,663 to Thompson for "Closed loop medicament pump."
U.S. Pat. No. 6,669,663 to Thompson for "Closed loop medicament pump."

Tables 2 through 11 below list drugs that may be employed in various embodiments of the present invention according to the general disease state they are intended to treat (e.g., bladder over-activity or stress incontinence), the effects or actions such drugs promote or cause, the applicable class(es) of drugs having such effects or actions, the names of some of the specific drugs falling within the scope of such drug class(es), and delivery sites for such drugs.

TABLE 2

| Drugs for Treatment of Bladder Over-Activity | | | |
| --- | --- | --- | --- |
| Action | Drug Class | Specific Drug | Delivery Site |
| Depress Bladder Contractions | Antimuscarinic (Anticloinergic) | Tolterodine, Trospium, Propantheline, Atropine, Hyoscyamine, Darifenacin, Solifenacin | Digestive system, central nervous system, pudendal nerves, sacral nerves, vascular system |
| Detrusor Muscle Inhibitor | Membrane channel drugs | Calcium Antagonists and | Digestive system, central nervous system, pudendal |

TABLE 2-continued

Drugs for Treatment of Bladder Over-Activity

| Action | Drug Class | Specific Drug | Delivery Site |
|---|---|---|---|
| | | Potassium Channel Openers | nerve, sacral nerves, vascular system |
| Mixed Mode | Antimuscarinic and channel blockers | Terodiline, oxybuynin, propiverine and flaxoxate | Digestive system, central nervous system, pudendal nerves, sacral nerves, vascular system |
| Detrusor Muscle Relaxant | Alpha Adrenoceptor Antagonists | Alfuzosin, Doxazosin, Prazosin, Terazosin, Tamsulosin | Digestive system, central nervous system, pudendal nerves, sacral nerves, vascular system |
| Detursor Inhibitor | Beta Adrenoceptor Agonists | Terbutaline, Chenbuterol, Salbutomol | Digestive system, central nervous system, pudendal nerves, sacral nerves, vascular system |
| Detursor Inhibitor, Blockade of Re-uptake of Serotonin and Noradrenaline | Antidepressants | Imipramine. | Digestive system, central nervous system, pudendal nerves, sacral nerves, vascular system |
| Prostatglandin Synthesis Inhibitors | Prostatglandin Synthesis Inhibitors | Indomethacin, Flurbiprofen | Digestive system, central nervous system, pudendal nerves, sacral nerves, vascular system |
| Motor Neuron Suppression | Motor Neuron Supression | Baclofen | Digestive system, central nervous system, pudendal nerves, sacral nerves, vascular system |
| Sensory | Sensory desensitization | Resiniferatoxin, Capsaicin | Bladder |
| Inflammation, Pain, Muscle Contractions | Inflammation, pain | Dimethyl Sulfoxide or bacillus Calmette-Guerin (BCG) | Bladder |
| Hormonal treatment | Hormone | Estrogen | Digestive system, central nervous system, pudendal nerves, sacral nerves, vascular system |

TABLE 3

Drugs for Treatment of Stress Incontinence

| Action | Drug Class | Specific Drug | Delivery Site |
|---|---|---|---|
| Alpha Adrenoceptor Antagonists | Alpha Adrenoceptor Antagonists | Ephedrine and Norephedrine | Digestive system, central nervous system, pudendal nerves, sacral nerves, vascular system, urethral sphincter and urethral muscle |
| Control of the Urethra | Beta Adrenoceptor Agonists | Propranolol | Digestive system, central nervous system, pudendal nerves, sacral nerves, vascular system, urethra |
| Contractility of the Urethra | Adrenaline and serotonin uptake inhibitor | Imipramine | Digestive system, central nervous system, pudendal nerves, sacral nerves, vascular system, urethra |
| External Urethral Sphincter Neural Activity Enhancer | Duloxetine | Duloxetine | Digestive system, central nervous system, pudendal nerves, sacral nerves, vascular system, urethra, urethral sphincter |
| Hormonal | Hormone | Estrogen | Digestive system, |

TABLE 3-continued

Drugs for Treatment of Stress Incontinence

| Action | Drug Class | Specific Drug | Delivery Site |
|---|---|---|---|
| Treatment | | | central nervous system, pudendal nerves, sacral nerves, vascular system, pelvic floor, urethra, bladder |

TABLE 4

Drugs for Treatment of Overflow Incontinence

| Action | Drug Class | Specific Drug | Delivery Site |
|---|---|---|---|
| Increase Bladder Sensitivity | Alpha-Adrenoceptor Antagonists | Alfuzosin, Doxazosin, Prazosin, Terazosin, Tamsulosin and Phenoxybenzamine. | Digestive system, central nervous system, pudendal nerves, sacral nerves, vascular system, bladder |
| Increase Bladder Sensitivity | Muscarinic Receptor Agonists | Bethanechol, Carbahol | Digestive system, central nervous system, pudendal nerves, sacral nerves, vascular system, bladder |
| Increase Bladder Sensitivity | Anticholinesterase Inhibitors | Distigmine | Digestive system, central nervous system, pudendal nerves, sacral nerves, vascular system, bladder |
| Hormonal Treatment | Hormone | Estrogen | Digestive system, central nervous system, pudendal nerves, sacral nerves, vascular system, pelvic floor, urethra, bladder |

TABLE 5

Interstitial Cystitis

| Action | Drug Class | Specific Drug | Delivery Site |
|---|---|---|---|
| Bacterial Elimination | Antibiotic | Flouroquinolones, Trimethoprimsulfamethoxazole | Digestive system, vascular system, prostate |
| Pain relief | Analgesic | Aspirin, acetaminophen, phenazopyridine, opioid medications such as meperidine, hydromorphone, methandone, levorphanol, morphine | Central nervous system, pudendal nerve, sacral nerves |

TABLE 6

Interstitial Cystitis

| Action | Drug Class | Specific Drug | Delivery Site |
|---|---|---|---|
| Bladder Lining Healing | Anti-inflammatory | Glucosamine, chondroitin and quercetin combination, hyaluronic acid, pentosan | Bladder |

TABLE 6-continued

Interstitial Cystitis

| Action | Drug Class | Specific Drug | Delivery Site |
|---|---|---|---|
| Pain Relief | Analgesic | polysulfate sodium, heparin sodium Aspirin, acetaminophen, phenazopyridine, opioid medications such as meperidine, hydromorphone, methandone, levorphanol, morphine | Central nervous system, pudendal nerve, sacral nerves |
| Bladder Antispasmodic | Tricyclic antidepressants | Amitriptyline, deipramine, nortriptyline, doxepin, imipramine | Bladder, sacral nerves, pudendal nerves |
| Bladder Antispasmodic | Muscle relaxant | Hyoscyamine, oxybutynin chloride, cyclobenzprine, hyoscyamine sulfate, baclofen | Bladder, pudendal nerves, sacral nerves, central nervous system |
| Urinary Urgency | Anticholinergic | Tolterodine tartrate | Bladder, pudendal nerve, sacral nerves, central nervous system |
| Pain | Sensory desensitization | Resiniferatoxin | Bladder |
| Inflammation, Pain, Muscle Contractions | Inflammation, pain | Dimethyl Sulfoxide or bacillus Calmette- | Bladder |
| Aid in Repair of Bladder Lining | Bladder lining | Guerin (BCG) Pentosan Polysufate Sodium | Bladder |
| Hormonal Treatment | Hormone | Estrogen | Central nervous system, pudendal nerves, sacral nerves, vascular system, pelvic floor, urethra, bladder |

TABLE 7

Fecal Incontinence/Irritable Bowel Syndrome

| Action | Drug Class | Specific Drug | Delivery Site |
|---|---|---|---|
| Diarrhea | Anti-diarrheal | Loperamide, alosetron | Digestive tract |
| Motility | Motility inhibition | Diphenoxylate, difenoxin, alosetron, cilansetron | Digestive tract |
| Motility | Motility stimulation | Tagaserod, cisapride, erythomycin, caffeine | Digestive Tract |
| Incontinence | Tricyclic antidepressant | Amitriptyline | Digestive Tract |

TABLE 8

Female Sexual Dysfunction

| Action | Drug Class | Specific Drug | Delivery Site |
|---|---|---|---|
| Libido, Vaginal Dryness, Sexual Arousal | | Sildenafil | Digestive system, vascular system, nervous system |
| Libido, Vaginal Dryness, Sexual Arousal | Hormone Replacement | Estrogen, testosterone | Digestive system, vascular system |
| Smooth Muscle Relaxant | Amino acid | L-arginine | Digestive system, vascular system |
| Smooth Muscle Relaxant, Increased Vaginal Blood Flow | Smooth Muscle Relaxant | Phentolamine | Digestive system, vascular system |
| Dopamine Activation | Orgasm, libido | Amantadine | Digestive system, vascular system, central nervous system, deep brain |
| Serotonin Re-uptake Inhibitor | Orgasm | Bupropion | Digestive system, vascular system, central nervous system, deep brain |
| Anti-anxiety | Orgasm, Libido | Buspione | Digestive system, vascular system, central nervous system, deep brain |
| Antiserotonergic | Orgasm, Libido | Cypropeptadine | Digestive system, vascular system, central nervous system, deep brain |
| Sympathomimetic | Orgasm | Dextroamphetamine | Digestive system, vascular system, central nervous system, deep brain |
| Sympathomimetic | Orgasm | Pemoline | Digestive system, vascular system, central nervous system, deep brain |
| Adrenergic Receptor Antagonist | Orgasm, Libido | Yohimbine | Digestive system, vascular system, central nervous system, deep brain |

TABLE 9

Erectile Dysfunction

| Action | Drug Class | Specific Drug | Delivery Site |
|---|---|---|---|
| Smooth Muscle Relaxant | Enzyme Inhibitor | Sildenafil, Vardenafil, Tadalafil, Yohimbine | Digestive system, vascular system, penis |
| Vascular Dilator, Smooth Muscle Relaxant | Vascular Dilator, Smooth Muscle Relaxant | Prostagladin, Phentolamine | Digestive system, vascular system, penis |
| Libido, Sexual Arousal | Hormone Replacement | Estrogen, testosterone | Digestive system, vascular system, penis |

TABLE 10

Premature Ejaculation

| Action | Drug Class | Specific Drug | Delivery Site |
|---|---|---|---|
| Delayed Ejaculation | Selective Serotonin Reuptake Inhibitor | Sertraline, Paroxetine | Digestive system, vascular system, central nervous system, penis |
| Delayed Ejaculation | Tricyclic Antidepressants | Clomipramine | Digestive system, vascular system, central nervous system, penis |

TABLE 11

Prostatitis

| Action | Drug Class | Specific Drug | Delivery Site |
|---|---|---|---|
| Bacterial Elimination | Antibiotic | Flouroquinolones, Trimethoprim-Sulfamethoxazole | Digestive system, vascular system, prostate |
| Pain relief | Analgesic | Aspirin, acetaminophen, phenazopyridine, opioid medications such as meperidine, hydromorphone, methandone, levorphanol, morphine | Central nervous system, pudendal nerves, sacral nerves |

Figure 11D:

FIGS. 11A through 11G show various embodiments of first and second electrical stimulation pulse regimes and first and second drug delivery regimes of the present invention. FIG. 11A illustrates an electrical stimulation pulse regime being applied to a first electrical stimulation site and a drug bolus being delivered to a first target tissue volume. One example where such an electrical pulse regime and drug delivery regime could be employed is periodic electrical stimulation to treat incontinence and the delivery of a patient-activated drug bolus for pain relief.

FIG. 11B shows periodic electrical stimulation applied to a first electrical stimulation site and periodic drug delivery to a first target tissue volume. One example where such an electrical pulse regime and drug delivery regime could be employed is periodic electrical stimulation to treat incontinence and periodic drug delivery to treat interstitial cystitis.

FIG. 11C shows periodic electrical stimulation applied to a first electrical stimulation site, periodic drug delivery to a first target tissue volume, and bolus drug delivery to a second target tissue volume. One example where such an electrical pulse regime and drug delivery regime could be employed is electrical stimulation for the treatment of incontinence, drug delivery for the treatment of pain, and the delivery of a patient-activated drug bolus to treat sexual dysfunction.

FIG. 11D shows periodic drug delivery to a first target tissue volume. One example where such a drug delivery regime could be employed is the delivery of one or more drugs to a target tissue volume for the treatment of prostatitis.

Figure 11E:

FIG. 11E shows continuous drug delivery to a target tissue volume. One example where such a drug delivery regime could be employed is the delivery of one or more drugs to the bladder for the treatment of interstitial cystitis.

Figure 11F:
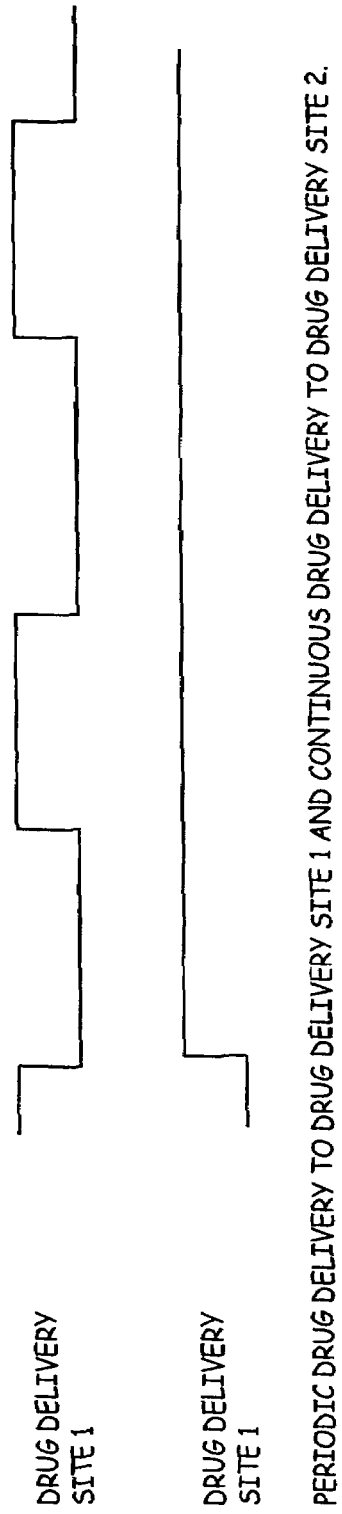

FIG. 11F shows periodic drug delivery to a first target tissue volume and continuous drug delivery to a second tissue volume. One example where such a drug delivery regime could be employed is the periodic delivery of a first drug for the treatment of pelvic pain and the continuous delivery of a second drug for the treatment of interstitial cystitis.

FIG. 11G shows periodic electrical stimulation being applied to a first electrical stimulation site, periodic electrical stimulation being applied to a second electrical stimulation site, and the delivery of a bolus of one or more drugs to a first target tissue volume. One example where such an electrical stimulation and drug delivery regime could be employed is periodic electrical stimulation at a first stimulation site for the treatment of fecal incontinence, periodic electrical stimulation at a second electrical stimulation site for the treatment of urinary incontinence, and the delivery of a patient-activated bolus of one or more drugs for the treatment of erectile dysfunction.

The various embodiments of the present invention described and shown thus far may be adapted and modified to permit the use of a number of different communication schemes. Accordingly, incorporated by reference herein, in its entirety, is U.S. Patent Application Publication No. 20020082665A1 to Haller et al. published Jun. 27, 2002 entitled "System and Method of Communicating between an Implantable Medical Device and a Remote Computer System or Health Care Provider," which patent application teaches methods and devices that may be adapted for use in some embodiments of the present invention. In the present invention it is contemplated that the methods and devices described hereinabove be extended to include the various communication systems of Haller et al. for, by way of example, one or more of monitoring the performance of INS 10 and/or an implantable drug pump implanted within the body of a patient, monitoring the health of the patient and remotely delivering an electrical stimulation and/or drug therapy to the patient through INS 10 and/or implantable or external drug pump 310, INS 10 and/or implantable or external drug pump 310 being capable of bi-directional communication with a communication module located external to the patient's body, the system comprising: (a) INS 10 and/or implantable or external drug pump 310; (b) a communication module; (c) a mobile telephone or similar device operably connected to the communication module and capable of receiving information therefrom or relaying information thereto; (e) a remote computer system, and (f) a communication system capable of bi-directional communication.

The preceding specific embodiments are illustrative of the practice of the invention. It is to be understood, therefore, that other expedients known to those skilled in the art or disclosed herein may be employed without departing from the invention or the scope of the appended claims.

In the claims, means plus function clauses are intended to cover the structures described herein as performing the recited function and their equivalents. Means plus function clauses in the claims are not intended to be limited to structural equivalents only, but are also intended to include structures which function equivalently in the environment of the claimed combination. All printed publications and patents referenced hereinabove are hereby incorporated by reference herein, each in its respective entirety.

The invention claimed is:

1. A method of treating at least one pelvic floor disorder, the at least one disorder being selected from a group consisting of prostatitis, prostatalgia and prostatodynia, the method comprising:
   delivering electrical stimulation from a medical device implanted within a patient diagnosed with the pelvic floor disorder to a pudendal nerve or branches or portions thereof of the patient via at least one electrode of a lead implanted within the patient proximate to the pudendal nerve or branches or portions thereof; and
   configuring the electrical stimulation to provide at least partial relief from the pelvic floor disorder.

2. The method of claim 1, further comprising diagnosing the patient as having the at least one pelvic floor disorder.

3. The method of claim 1,
   wherein the lead comprises a first lead and the electrical stimulation comprises first electrical stimulation, and
   wherein the method further comprises:
   delivering second electrical stimulation from the medical device to one of the pudendal nerve, another pudendal nerve, a sacral nerve, or branches or portions thereof of the patient via at least one electrode of a second lead implanted proximate to the pudendal nerve, another pudendal nerve, a sacral nerve, or branches or portions thereof; and
   configuring a combination of the first and second electrical stimulation to provide at least partial relief from the pelvic floor disorder.

4. The method of claim 3, wherein delivering first electrical stimulation comprises delivering the first electrical stimulation to the pudendal nerve or branches or portions thereof on a first side of the patient, and delivering second electrical stimulation comprises delivering the second electrical stimulation to the other pudendal nerve on a second side of the patient.

5. The method of claim 3, wherein delivering second electrical stimulation comprises delivering the second electrical stimulation to the sacral nerve or branches or portions thereof.

6. The method of claim 5, wherein delivering the first electrical stimulation to the pudendal nerve or branches or portions thereof comprises delivering the first electrical stimulation to the pudendal nerve or branches or portions thereof on a first side of the patient, and delivering the second electrical stimulation to the sacral nerve or branches or portions thereof comprises delivering the second electrical stimulation to the sacral nerve or branches or portions thereof on a second side of the patient.

7. The method of claim 3, wherein delivering the first and second electrical stimulation comprises initiating delivery of the second electrical stimulation while the first electrical stimulation is already being delivered and in response to a sensed physical parameter or symptom.

8. The method of claim 1, wherein the at least one pelvic floor disorder comprises prostatitis.

9. The method of claim 1, wherein the at least one pelvic floor disorder comprises prostatalgia.

10. The method of claim 1, wherein the at least one pelvic floor disorder comprises prostatodynia.

11. The method of claim 1, wherein the lead comprises a lead body less than about 1.5 mm in diameter.

12. The method of claim 1, wherein an inter-electrode distance of the lead is selected from the group consisting of about 1 mm, about 2 mm, about 3 mm, about 4 mm, and about 5 mm, about 6 mm, about 7 mm, about 8 mm, about 9 mm, and about 10 mm.

13. The method of claim 1, wherein the at least one electrode of the lead has an electrode surface area ranging between about 4.0 sq. mm and about 25 sq. mm.

14. The method of claim 1, wherein a distance between proximal and distal ends of at least one of the first lead and the second lead is selected from a group consisting of about 6 inches, about 8 inches, about 10 inches, about 12 inches, about 14 inches, about 16 inches about 18 inches, about 20 inches and more than about 20 inches.

15. The method of claim 1, wherein the electrical stimulation has a frequency ranging between about 50 Hz and about 100 Hz.

16. The method of claim 1, further comprising at least one of activating, modifying or terminating the electrical stimulation in response to a physical parameter or symptom being sensed.

17. The method of claim 16, further comprising sensing the physical parameter using a sensor selected from the group consisting of a nerve electrical signal sensor and an electromyographic sensor.

18. The method of claim 1, further comprising delivering a drug to the patient via a drug pump implanted within the patient.

* * * * *